United States Patent
Varadan et al.

(10) Patent No.: US 10,653,316 B2
(45) Date of Patent: May 19, 2020

(54) ROLL-TO-ROLL MANUFACTURING METHOD OF WIRELESS NANOSENSOR

(71) Applicant: NANOWEAR INC., Brooklyn, NY (US)

(72) Inventors: Vijay K. Varadan, State College, PA (US); Pratyush Rai, State College, PA (US); Se Chang Oh, State College, PA (US)

(73) Assignee: NANOWEAR INC., Brooklyn, NY (US)

( * ) Notice: Subject to any disclaimer, the term of this patent is extended or adjusted under 35 U.S.C. 154(b) by 0 days.

(21) Appl. No.: 16/259,593

(22) Filed: Jan. 28, 2019

(65) Prior Publication Data

US 2019/0216320 A1     Jul. 18, 2019

Related U.S. Application Data

(63) Continuation of application No. 15/425,360, filed on Feb. 6, 2017, now Pat. No. 10,231,623.
(Continued)

(51) Int. Cl.
*H05K 3/30*     (2006.01)
*A61B 5/00*     (2006.01)
(Continued)

(52) U.S. Cl.
CPC .......... *A61B 5/0022* (2013.01); *A61B 5/6802* (2013.01); *B41F 17/00* (2013.01);
(Continued)

(58) Field of Classification Search
CPC ...... B41F 17/38; B41F 17/00; H01L 51/0566; Y10T 29/49126; Y10T 29/4913;
(Continued)

(56) References Cited

U.S. PATENT DOCUMENTS 4,363,930 A    12/1982 Hoffman
4,367,752 A    1/1983 Jimenez et al.
(Continued)

OTHER PUBLICATIONS

Rai, Pratyush, "Hybrid Nanostructured Textile Bioelectrode for Unobtrusive Health Monitoring" (Aug. 2013). Theses and Dissertations. 893 (Year: 2013).
(Continued)

*Primary Examiner* — Donghai D Nguyen
(74) *Attorney, Agent, or Firm* — Davidson, Davidson & Kappel, LLC

(57) ABSTRACT

A roll-to-roll printing process for large scale manufacturing of nanosensor systems for sensing pathophysiological signals is disclosed. The roll-to-roll manufacturing process may include three processes to improve the throughput and to reduce the cost in manufacturing: fabrication of textile based nanosensors, printing conductive tracks, and integration of electronics. The wireless nanosensor systems can be used in different monitoring applications. The fabric sheet printed and integrated with the customized components can be used in a variety of different applications. The electronics in the nanosensor systems connect to remote severs through adhoc networks or cloud networks with standard communication protocols or non-standard customized protocols for remote health monitoring.

20 Claims, 18 Drawing Sheets

Related U.S. Application Data

(60) Provisional application No. 62/291,126, filed on Feb. 4, 2016.

(51) Int. Cl.

| | | |
|---|---|---|
| *H05K 1/03* | (2006.01) | |
| *H01L 51/05* | (2006.01) | |
| *B41F 17/00* | (2006.01) | |
| *B41F 17/38* | (2006.01) | |
| *G16H 40/67* | (2018.01) | |
| *G06F 19/00* | (2018.01) | |
| *A61B 5/024* | (2006.01) | |
| *A61B 5/04* | (2006.01) | |
| *A61B 5/0496* | (2006.01) | |
| *A61B 5/053* | (2006.01) | |
| *A61B 5/11* | (2006.01) | |
| *H05K 1/18* | (2006.01) | |

(52) U.S. Cl.
 CPC .............. *B41F 17/38* (2013.01); *G06F 19/00* (2013.01); *G16H 40/67* (2018.01); *H01L 51/0566* (2013.01); *H05K 1/038* (2013.01); *A61B 5/02427* (2013.01); *A61B 5/04004* (2013.01); *A61B 5/0496* (2013.01); *A61B 5/0531* (2013.01); *A61B 5/11* (2013.01); *A61B 5/1112* (2013.01); *A61B 5/6803* (2013.01); *A61B 5/6804* (2013.01); *A61B 5/725* (2013.01); *A61B 2562/0204* (2013.01); *A61B 2562/0285* (2013.01); *A61B 2562/12* (2013.01); *H05K 1/189* (2013.01); *H05K 2201/10151* (2013.01); *H05K 2201/10166* (2013.01); *H05K 2203/1545* (2013.01); *Y10T 29/4913* (2015.01)

(58) Field of Classification Search
 CPC ...... Y10T 29/49155; H05K 2203/1545; H05K 1/189; H05K 2201/10151; A61B 2562/12; A61B 2562/0285; A61B 5/0022; A61B 5/6802
 USPC .......................................... 29/830, 832, 846
 See application file for complete search history.

(56) References Cited

U.S. PATENT DOCUMENTS

| | | | |
|---|---|---|---|
| 4,406,850 A * | 9/1983 | Hills ........................ | D01D 5/34 264/169 |
| 4,682,415 A | 7/1987 | Adell | |
| 5,114,744 A * | 5/1992 | Cloutier ................. | H05K 3/102 347/1 |
| 5,162,074 A * | 11/1992 | Hills ........................ | D01D 4/06 216/83 |
| 5,501,229 A | 3/1996 | Sekler et al. | |
| 5,749,365 A | 5/1998 | Magill | |
| 5,802,607 A | 9/1998 | Triplette | |
| 5,851,562 A * | 12/1998 | Haggard ................. | D01D 1/065 425/131.5 |
| 5,853,005 A | 12/1998 | Scanlon | |
| 6,047,203 A | 4/2000 | Sackner et al. | |
| 6,662,032 B1 | 12/2003 | Gavish et al. | |
| 6,687,523 B1 | 2/2004 | Jayaramen et al. | |
| 7,136,693 B2 | 11/2006 | Brodnick | |
| 7,163,659 B2 * | 1/2007 | Stasiak .............. | G01N 27/3278 422/68.1 |
| 7,319,895 B2 | 1/2008 | Klefstad-Sillonville et al. | |
| 7,354,877 B2 | 4/2008 | Rosenberger et al. | |
| 7,390,760 B1 | 7/2008 | Chen et al. | |
| 7,559,902 B2 | 7/2009 | Ting et al. | |
| 7,592,276 B2 | 9/2009 | Hill | |
| 7,857,777 B2 | 12/2010 | Larson et al. | |
| 7,862,624 B2 | 1/2011 | Tran | |
| 7,871,700 B2 | 1/2011 | Poulin et al. | |
| 9,103,654 B1 | 8/2015 | Cox | |
| 9,421,134 B2 | 8/2016 | Schlinz | |
| 10,131,993 B2 * | 11/2018 | Varadan .................. | C23C 18/31 |
| 2005/0034485 A1 | 2/2005 | Klefstad-Sillonville et al. | |
| 2006/0024499 A1 | 2/2006 | Kim et al. | |
| 2006/0175581 A1 | 8/2006 | Douglas | |
| 2006/0252999 A1 | 11/2006 | Devaul et al. | |
| 2006/0282021 A1 | 12/2006 | Devaul et al. | |
| 2007/0049842 A1 | 3/2007 | Hill et al. | |
| 2007/0120297 A1 | 5/2007 | Weider | |
| 2008/0083740 A1 | 4/2008 | Kaiserman | |
| 2008/0139911 A1 | 6/2008 | Chandrasekaran et al. | |
| 2008/0287769 A1 | 11/2008 | Kurzweil et al. | |
| 2009/0024017 A1 | 1/2009 | Ruffini et al. | |
| 2009/0088652 A1 | 4/2009 | Tremblay | |
| 2009/0306485 A1 | 12/2009 | Bell | |
| 2010/0185398 A1 | 7/2010 | Berns et al. | |
| 2010/0198038 A1 | 8/2010 | Nagata | |
| 2010/0273049 A1 | 10/2010 | Vidal et al. | |
| 2010/0274100 A1 | 10/2010 | Bahar et al. | |
| 2011/0004088 A1 | 1/2011 | Grossman | |
| 2011/0260115 A1 | 10/2011 | Kim | |
| 2013/0281795 A1 | 10/2013 | Varadan | |
| 2013/0281815 A1 | 10/2013 | Varadan | |
| 2016/0222539 A1 | 8/2016 | Varadan et al. | |

OTHER PUBLICATIONS

Lao et al. "Hierarchical Oxide Nanostructures" J. Mater. Chem., 14, 770-773. Oct. 23, 2003.

May 6, 2015 Office Action issued in the U.S. Appl. No. 13/829,898.

Uberoi, et al., Interpretation of the Electrocardiogram of Young Athletes, Circulation, 124: 746-757 (2011).

Nov. 13, 2014 Office Action issued in U.S. Appl. No. 13/829,898.

American Heart Association, "Heart Rate Variability: Standards of Measurement, Physiological Interpretation, and Clinical Use" Circulation. 1996; 93: 1043-1065.

Dekker et al., "Heart Rate Variability from Short Electrocardiographic Recordings predicts Mortality from All Causes in Middle-Aged and Elderly Men" American Journal of Epidemiology, vol. 145, No. 10, 1997, 899-908, http:aje.oxfordjournals.org/accessed on Oct. 25, 2012.

Huei et al., "Develop an efficient Electrode to detect ECG signal" download from the internet prior to Aug. 19, 2011.

Hulley et al., "Randomized Trial of Estrogen Plus Progestin for Secondary Prevention of Coronary Heart Disease in Postmenopausal Women" Estrogen Plus Progestin and CHD, JAMA Aug. 19, 1998—vol. 280, No. 7 (9 pages).

Indiareport, "Now a vest that tracks medical condition" dated Oct. 12, 2011, http://www.indiareport.com/news-details/print_news.php?id=11 . . . accessed Oct. 13, 2011 (1 page).

Jahrsdoerfer et al., "Clinical Usefulness of the EASI 12-Lead Continuous Electrocardiographic Monitoring System" CritCare Nurse 2005; 25:28-37, ccn.aacnjournals.org, accessed on Oct. 25, 2012.

Kleber, "ST-segment elevation in the electrocardiogram: a sign of myocardialischemia" Cardiovascular Research 45 (2000) 111-118.

Leicht et al., "Heart rate variability and endogenous sex hormones during the menstrual cycle in young women" Experimental Physiology, Manuscript received Nov. 28, 2002, ep.physoc.org, accessed Oct. 25, 2012 (6 pages).

Leonarduzzi et al., "Wavelet Leader Based Multifractal Analysis of heart Rate Variability during Myocardial Ischemia" 32nd Annual International Conference of the IEEE EMBS Buenos Aires, Argentina, Aug. 31-Sep. 4, 2010 (4 pages).

Llyod-Jones et al., "Heart Disease and Stroke Statistics—2010 Update, a Report from the American Heart Association" Circulation, http//circ.ahajournals.org/accessed on Oct. 25, 2012.

Narayan., "T-Wave Alternans and the Susceptibility to Ventricular Arrhythmias" Journal of the American College of Cardiology, vol. 47, No. 2, 2006, 269-281.

Nussmeier "The female perspective: Gender in cardiothoracic surgery" The Journal of Thoracic and Cardiovascular Surgery, Sep. 2003, 126: 618-9.

(56) References Cited

OTHER PUBLICATIONS

Pan et al., "A Real-Time QRS Detection Algorithm" IEEE Transactions on Biomedical Engineering, 328.
Rudinac et al., "Fractal and Multifractal Analysis of heart Rate Variability " Telsiks, Sep. 26-28, 2007, 325-328.
Scanlon, "Acoustic Sensor Pad for Physiology Monitoring" Proceedings—19th International Conference—IEEE/EMBS Oct. 30-Nov. 2, 1997 (4 pages).
Tabibiazar et al., "Silent Ischemia in People with Diabetes: A Condition That Must Be Heard" Clincal Diabetes, vol. 21, No. 1, 2003 (5pages).
Varadan et al. "e-bra with Nanosensors for Real Time Cardiac Health Monitoring and Smartphone Communication" journal of Nanotechnology in Engineering and Medicine, May 1, 2011, vol. 2 (7 pages).
Varadan et al. "e-Nanoflex Sensor System: Smartphone-Based Roaming Health Monitor" Journal of Nanotechnology in Engineering and Medicine Feb. 1, 2010, vol. 2 (11 pages).
Varadan, "Wireless Point-of-Care Diagnosis for Sleep Disorder With Dry Nanowire Electrodes" Journal of Nanotechnology in Engineering and Medicine Aug. 2010, vol. 1 (11 pages).
Varadan, "Am EKG in your Underwear. Nanostructured sensors, smartphones, and cloud computing promise a new platform everyday medical morning." Mechanical Engineering Magazine, http://memagazine.asme.org/Articles/2011/October/EKG_Underwear.cfm? PrintPage=yes, accessed Oct. 14, 2011 (5pages).
Zhang et al. "Pulse Transit-Time based Blood pressure Estimation Using Hilbert-Huang Transform" 31st Annual International Conference of the IEEE EMBS Minneapolis, Minnesota, USA, Sep. 2-6, 2009 (4pages).
Vijay K. Varadan; Prashanth S. Kumar; Sechang Oh; Gyanesh N. Mathur; Pratyush Rai; Lauren Kegley; E-bra with nanosensors, smart electronics and smart phone communication network for heart rate monitoring. Proc. SPIE 7980, Biosensors, and Info-Tech Sensors and Systems 2011, 79800S (Apr. 13, 2011); doi:10.1117/12.885649.
Growth of highly oriented carbon nanotubes by plasma-enhanced hot filament chemical vapor deposition Huang, Z. P. and Xu, J. W. and Ren, Z.F. and Wang, J. H. and Seigal, M. P. and Provencio, P. N., Applied Physics Letters, 73, 3845-3847 (1998), DOI:http://dx.doi.org/10.1063/1. 122912.
Bordjiba, Mohamed Mohamedil and Le H Dao. Binderless carbon nanotube/carbon fibre composites for electrochemical micropower sources. nanotechnology, vol. 18, No. 3 Published Jan. 3, 2007.
Jun. 10, 2015 Office Action issued in U.S. Appl. No. 13/449,755.
Kong et al., "Spontaneous Polarization-Induced Nanohelixes, Nanosprings, and Nanorings of Peizoelectric Nanobelts" Nano. Lett. vol. 3, 12 1625-1631 (2003).
Nov. 13, 2014 Office Action issued in U.S. Appl. No. 13/449,755.
Zhou, Zhengping and Wu, Xiang-Fa and Fong, Hao. Electrospun carbon nanofibers surface-grafted with vapor-grown carbon nanotubes as hierarchical electrodes for supercapacitors, Applied Physics Letters, 100, 023115 (2012).
U.S. Appl. No. 13/499,755, filed Feb. 6, 2014 (3 pages).
U.S. Appl. No. 13/449,755, filed Jul. 2, 2014 (18 pages).
Pan et al., "A Real-Time QRS Detection Algorithm" IEEE Transactions on Biomedical Engineering, vol. BME-32. No. 3 Mar. 1985, 230-236.
U.S. Appl. No. 13/449,755, filed Jul. 3, 2013 (19 pages).
Yan et al. (Helical Polyaniline Nanofibers Induced by Chiral Dopants by a Polymerization Process. Advanced Mateirals. 2007, 19, 3353-3357).
Kim et al. (Fabrication of carbon nanofiber, Cu Composite powder by electroless plating and microstructural evolution during thermal exposure, Scripta Materialia, vol. 52, Issue 10, May 2005, pp. 1045-1049).
Park et al. (Growth and high current field emission of carbon nanofiber films with electroplated Ni catalyst, Diamond and Related Materials, vol. 14, issues 11-12, Nov.-Dec. 2005, pp. 2094-2098).
McGary et al. (Magnetic nanowires for acoustic sensors, J. Appl. Phys. 99, 088310 (2006).
United Sates Patent and Trademark Office Final Rejection for U.S. Appl. No. 13/499,755 dated Dec. 27, 2013 (18 pages).

\* cited by examiner

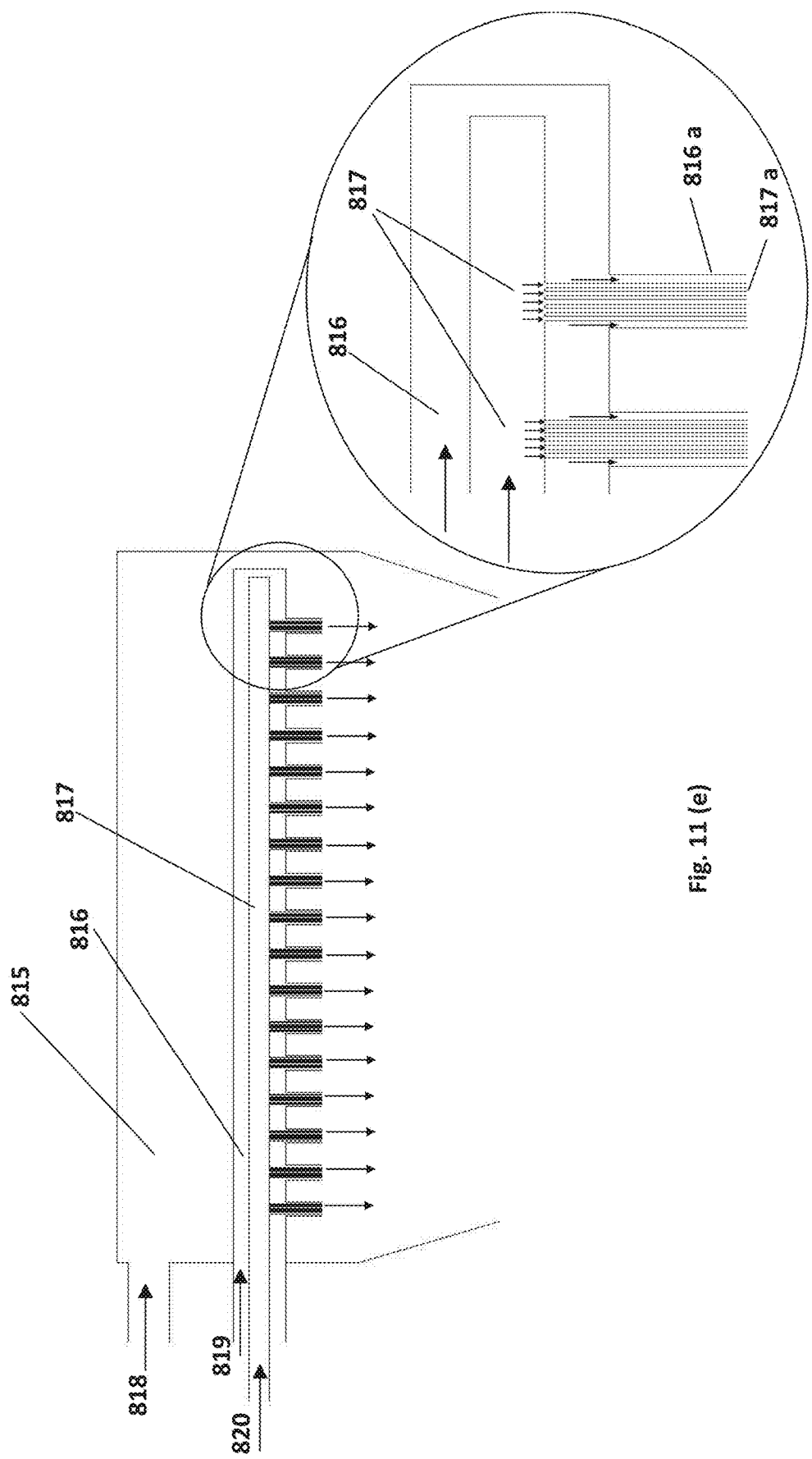

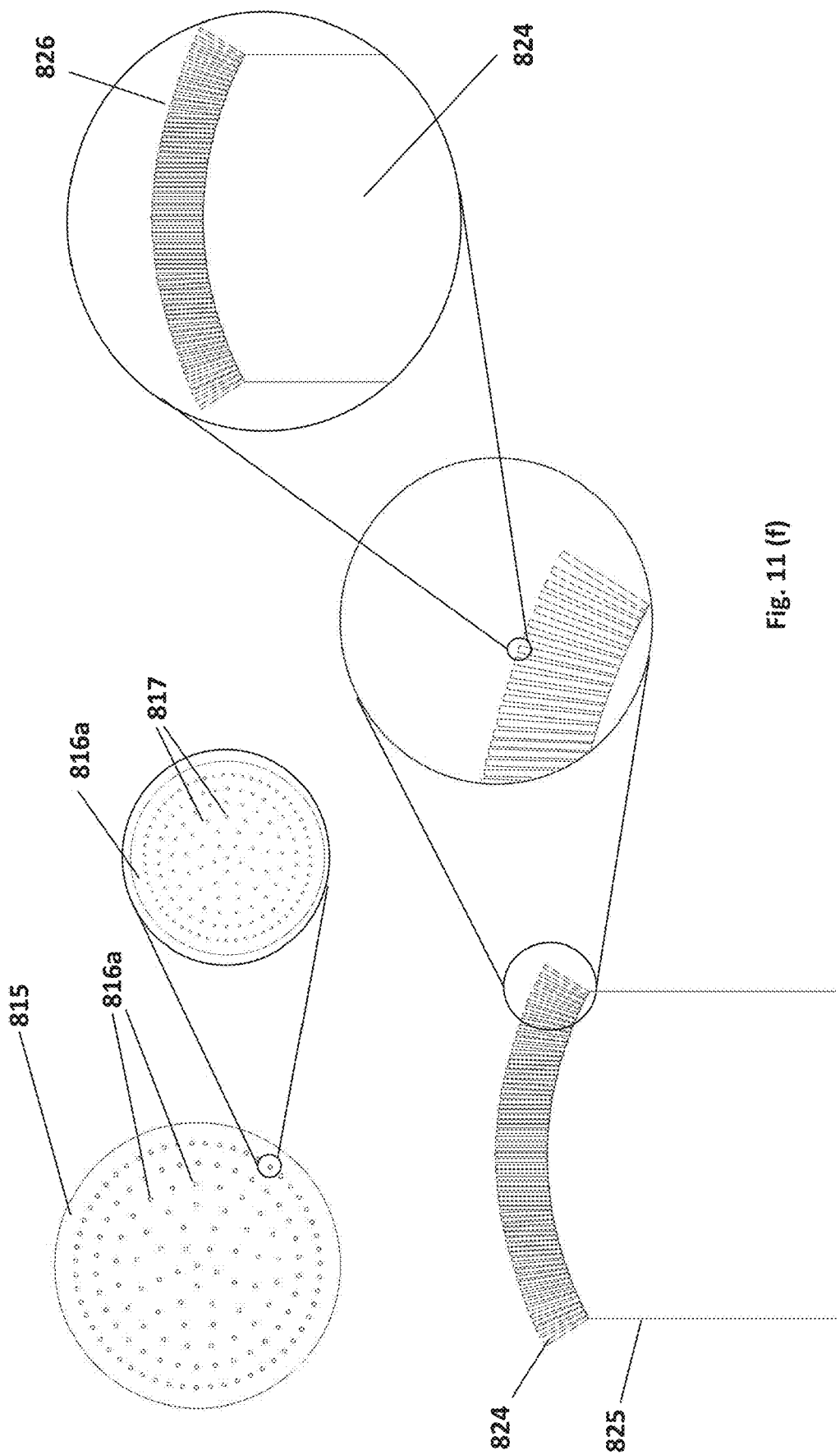

ROLL-TO-ROLL MANUFACTURING METHOD OF WIRELESS NANOSENSOR

This application is a continuation of U.S. application Ser. No. 15/425,360, filed Feb. 6, 2017, Now U.S. Pat. No. 10,231,623 which claims the benefit of U.S. Provisional Patent Application No. 62/291,126, filed Feb. 4, 2016, the disclosures of which are hereby incorporated by reference in their entirety.

CROSS-REFERENCE TO RELATED APPLICATION

This application is related to U.S. Provisional application Ser. Nos. 14/995,334, 62/291,088 and 62/104,686, each entitled Large Scale Manufacturing of Hybrid Nanostructured Textile Sensors, the entire disclosures of which are hereby incorporated by reference.

BACKGROUND

Conventional large scale textile manufacturing processes like screen printing involve different methodologies at each stage that are handled by individual units. These processes involve a high resource drain in terms of cost, labor, time and space. Large scale manufacturing of sensor systems on textiles can be performed using individual equipment and processes for screen printing or stitching of the sensors and conductive tracks, and soldering and mounting connectors for electronics. See, for example, Varadan et al, e-Nanoflex Sensor System:Smartphone-Based Roaming Health Monitor, Journal of Nanotechnology in Engineering and Medicine (2011).

SUMMARY OF THE INVENTION

In accordance with certain embodiments of the present invention as disclosed herein, a continuous process is provided, where an optimized roll-to-roll process is used to manufacture textiles including but not limited to sensors, conductive tracks, flexible circuits and connectors to increase the throughput efficiency and to reduce the cost. The roll-to roll process may employ, for example, a rotogravure printing machine.

In accordance with an embodiment of the present invention, a method for manufacturing a wireless nanosensor monitoring system is provided. The method includes providing a roll-to-roll printing process for use on a fabric substrate; providing a fabric; printing an insulating base layer onto the fabric; printing a conductive track layer on top of the insulating base layer; printing an insulating cover layer on top of the conductive track layer; printing at least one sensor onto the fabric or another fabric; connecting the at least one sensor to the conductive track layer; mounting and bonding electronics onto the fabric surface; and connecting the electronics to the conductive track layer to form the wireless nanosensor system. Preferably, this process is continuous. The steps of printing at least one sensor onto the fabric and connecting the at least one sensor to the conductive track layer may be performed by printing an adhesive onto the fabric at a location along the conductive track and depositing vertically aligned nanostructures on the adhesive to provide a sensor connected to the conductive track layer. The vertically aligned nanostructures may include one dimensional and/or three dimensional structures.

In accordance with further aspects of this embodiment, the method does not constrain the direction/orientation or the density using a template. The direction/orientation of nanostructures and number of nanostructures deposited on the adhesive are both governed by an electrostatic field applied between activated nanostructure and the adhesive substrate on the roll, or through a pneumatic force imparted on the nanostructure material. Further, the deposition of nanostructures does not require stoppage of the rotogravure printing machine. Nanostructures can be deposited either using an electrostatic field or pneumatic force as substrate is fed through the roll.

Further, with regard to layouts of the circuits on the fabric, desired circuit layouts are printed on the same substrate film in a sequential manner. There is no need to perform via hole punching lamination, via filling and other processes. Automated mechanisms of placement of components that may be sensors or electronic components can be performed using robotic assemblies and thermal bonding/cold solder.

Further, the at least one sensor may be configured to detect pathophysiological signals from a wearer of the wireless nanosensor monitoring system. The at least one sensor may be printed onto the fabric in an array. The at least one sensor may include vertically aligned nanostructures deposited on an adhesive. The electronics are configured to receive a signal from the at least one sensor. The signal is transmitted wirelessly to a receiver or cloud network for remote monitoring. Alternatively the electronics can be configured to transmit the signal through a cable to computing equipment for monitoring or analysing the signal. The electronics may include a breakout circuit. The breakout circuit is connected to the conductive tracks by using a cold solder.

The insulating base layer may include an insulating polymer. The insulating base layer may include at least one of poly vinyl, poly acrylate or polyurethane polymer. The conductive layer may include nanoparticles. The nanoparticles may be at least one of a silver nanoparticles or a carbon nanotube-polymer dispersed in a binder polymer which may include a poly vinyl, poly-acrylate or polyurethane base binder. The insulating cover may include an electrically insulating polymer. The electronics may be printed using at leak one organic semiconductor. Electronics can be printed by using organic semiconductors such as pentacene, pentacene-carbon nanotube composite and poly-3hexylthiophene, along with polymer dielectric materials such as poly(4-vinylphenol) The at least one organic semiconductor may be configured as a thin film transistor. The break out circuit may be a magnetic connector.

BRIEF DESCRIPTION OF THE DRAWINGS

Various embodiments are disclosed, by way of example only, with reference to the accompanying schematic drawings in which corresponding reference symbols indicate corresponding parts, in which:

FIGS. 11(a)-(f) illustrate spinnerets for use in the process of FIGS. 10(a) and 10(b).

DETAILED DESCRIPTION

Figure 1:
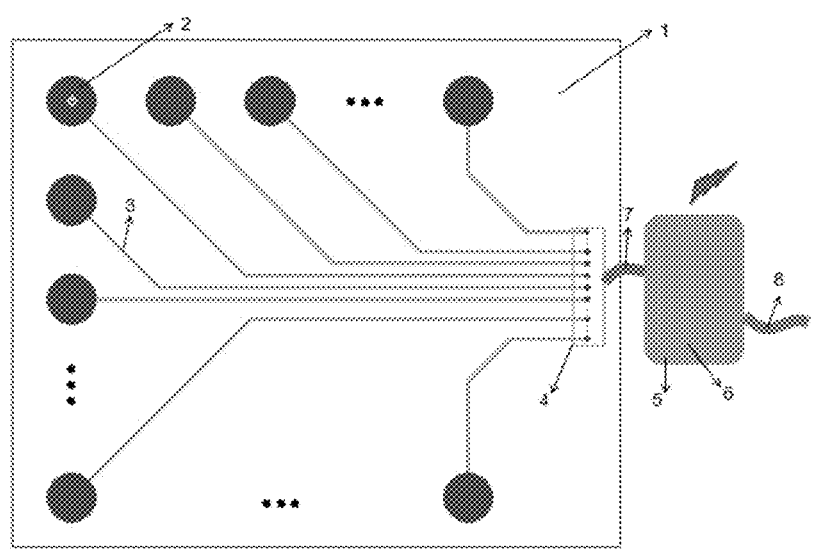
FIG. 1 shows a diagram of a nanosensor system according to one embodiment of the present invention.

The present disclosure provides a roll-to-roll process for manufacturing a wireless nanosensor system for health monitoring. FIG. 1 shows a diagram of a nanosensor system in accordance with an embodiment of the present invention. The nanosensor system is comprised of sensors, conductive tracks and connectors. Nanosensors 2 are printed nanosensors that are used in sensing pathophysiological signals. The nanosensors 2 are printed and/or bonded onto a fabric 1 in an array. Conductive tracks 3 are printed in or on the fabric 1 and are used to relay the sensed signal from the sensor to electronics 5 through a connector 4. The connection between the fabric and electronics can be established by directly attaching the connector 4 and a connector 6 together or through conductive wires 7. Signals are received in electronics 5and are processed and stored or transmitted wirelessly to a receiver or cloud network for remote monitoring. The electronics 5 can also be connected to computing equipment via cables 8 to monitor or analyze the signals. The pattern and configuration of sensors, conductive tracks, and a break out circuit/connector 4 can be customized according to various applications. The fabric 1includes a customized pattern of the nanosensors 2, the conductive tracks 3, and an integrated break out circuit. The fabric sheet including finally customized patterned sensors and the conductive tracks, and the integrated break out circuit and the electronics, all prepared by a roll-to-roll process, can then be cut for different applications, such as garments, bed sheets, wrist band, head band, chest band, arm band, gloves, cap/hat, and socks for a nanosensor system.

The nanosensor system that is fabricated by an embodiment of the roll-to-roll manufacturing process invention preferably includes: fabric 1, nanosensors 2, conductive tracks 3, break out circuit/connector 4, and electronics 5.

Two/three component yarn, which has polymer nanofibers embedded in a matrix of another polymer, can be used in fabrication of the nanosensor 2. Embedded nanofibers can be released by dissolving the matrix polymer. Fabrication of free standing nanostructures on fabric can be done by electrostatic or pneumatic deposition of two/three component yarn followed by dissolving the matrix polymer. The deposition is site specific because it is defined by the pattern of adhesive printed on fabric 1. The deposition processes can be done in two ways: a) with nanostructured fibers pre-coated with conductive material such as silver, gold, platinum, polyaniline, polypyrrole, poly(3,4-ethylenedioxythiophene) and rendered conductive or b) with nanostructured fibers not coated with conductive material and coated with conductive material later. For example, precoated nanostructured fibers can be prepared prior to the deposition process by batch spray coating the fibers, or by coating vertically freestanding nanostructured fibers on a dissolvable substrate followed by release of the fibers by dissolving the substrate. Alternatively, nanostructured fibers can be deposited by the deposition process and then coated later, for example, by an electroless plating process. These processes will be discussed in further detail below.

The sensor shapes/patterns may be circular, oval, clover leaf or fractal carpet of sensors. Such shapes can be used to achieve better contact on contoured interface such as fabric touching the human body. A nanosensor can be connected by conductive tracks to the wireless communication module to form a wireless nanosensor system. The fabric 1 can include customized patterned sensors and the conductive tracks, and the integrated break out circuit and the electronics fabricated by roll-to-roll process. The fabric can be cut out for different applications, such as health monitoring garments, bed sheets, wrist bands, head bands, chest bands, arm bands, gloves, and socks.

Conductive tracks that are printed on the fabric 1 may include or consist of 3 layers: a base insulation layer, a conductive layer and a covering insulation layer. The base layer may include electrically insulating polymer material such as poly vinyl based, poly acrylate or polyurethane polymer. The conductive layer may include nanoparticles such as silver nanoparticles or carbon nanotube-polymer nanocomposite dispersed in binder polymer such as poly vinyl, poly-acrylate or polyurethane based binders. The covering insulation layer may include electrically insulating polymer material such as poly vinyl based, poly acrylate or polyurethane polymer.

The printed pattern of conductive tracks 3 are drawn (located) to make connections between the nanosensors 2 and the breakout circuit/connector 4.

The electrical insulation material, used as the base and the cover insulation layer, can be selected by evaluating various polymeric formulations such as poly vinyl based, poly acrylate or polyurethane based polymers. The films made from these materials can be evaluated by testing their dielectric strength, durability under stress and torsion, water ingress protection and curing process. A formulation can be adapted to gravure printing process by controlling viscosity and use of solvents.

More complex electronics can be printed by using organic semiconductors such as pentacene, pentacene-carbon nanotube composite and poly-3 hexylthiophene, along with polymer dielectric materials such as poly(4-vinylphenol) to make thin film transistors (TFTs). Electrical circuits printed with different configurations of these TFTs can be used for applications such as temperature sensing by using temperature sensitivity of the semiconductor channel, strain sensing by using change in conductivity due to strain in semiconductor channel and inter-digitated electrodes for capacitive sensing that can be tuned to measure biopotential signals such as EKG.

The break out circuit/connector 4 may be connected to the conductive tracks 3 by using cold soldering options such as silver epoxy using precision dispensing gun. The break out circuit/connector 4 are designed to provide electrical connection and mechanical support to the electronics 5. The connectors 4 may be connected using magnetic force of attraction and connection is retained using a latching mechanism.

Figures 2A, 2B:
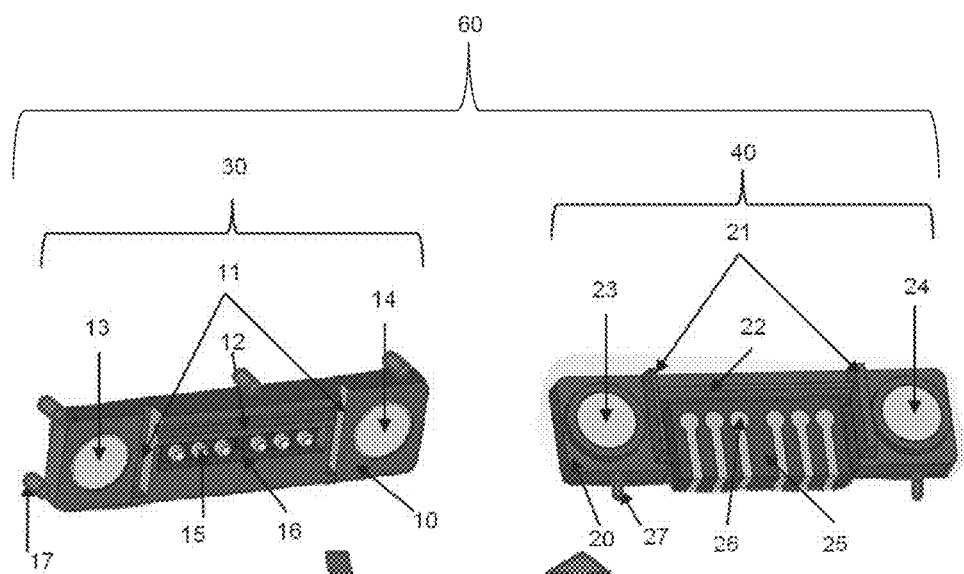
FIG. 2a shows a plain view of a plug part of a magnetic connector.
FIG. 2b shows a plan view of a receptacle part of a magnetic connector.
Figure 2C:
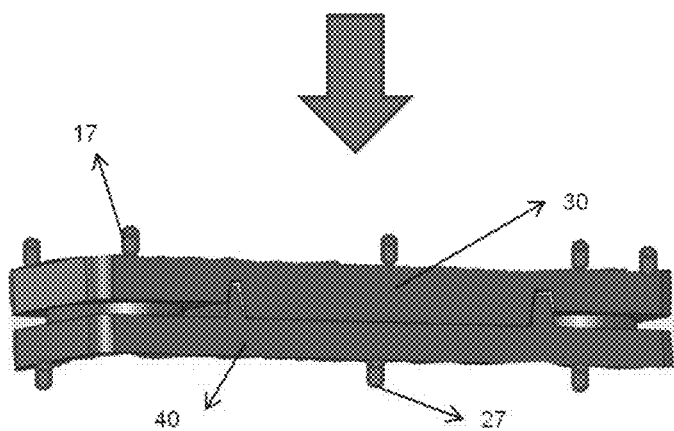
FIG. 2c shows a side view of two magnetic connectors interlocking.

In accordance with an embodiment, the break out circuit/connector 4 is a magnetic connector 60 shown in FIGS. 2a, 2b, and 2c. The magnetic connector 60 includes a plug part 30 and a receptacle part 40. The receptacle part 40 is secured to the fabric 1, for example, via an adhesive, with the electrical connections made, for example, in the same manner described herein for other electrical components.

FIGS. 2a and 2b shows the plug part 30 and the receptacle part 40 of the magnetic connector 60. FIG. 2c shows the magnetic connector 60 with the plug part 30 and receptacle part 40 connected in an interlocking manner.

The plug part 30 of the magnetic connector 60 may include three releasably secured parts including a case 10, magnets 13, 14 and pogo pins 15 wherein each part can be separated from the other parts in order to replace parts. The parts may be releasably secured, for example, via a press fit, a mating fit, or any other manner known in the art. The case 10 may include vertical groove 11, horizontal groove 12, widow 16 and alignment pin 17.

The receptacle part 40 of the magnetic connector 60 may include three releasably secured parts including a case 20, magnet 23, 24 and a printed circuit board (PCB) 25 wherein each part can be separated from each other in order to replace parts. The case 20 may include a vertical ridge 21, a horizontal ridge 22, and an alignment pin 27. The vertical ridge 21 and the horizontal ridge 22 of case 20 correspond respectively to the vertical groove 11 and the horizontal groove 12 of case 10.

The plug part 30 of the magnetic connector 60 includes case 10, magnets 13, 14 and at least one pogo pin 15. The attractive force between magnets 13 and 14 in conjunction with magnets 23 and 24 of the magnetic connector 60, located end the axial ends of plug part 30 and receptacle part 40 respectively allows the parts 30 and 40 to be securely mated to connect plug part 30 to receptacle part 40.

The magnets 13, 24 and 14, 23 are assembled with opposite polarities facing each other respectively, at the connected state. This provides self-aligning functionality between the plug part 30 and the receptacle part 40 because any misalignment will cause the magnets to repel. Magnets 13, 14 on the plug part 30 are replaceable in the event they lose their magnetic force after prolonged use. The magnetic connector 60 can provide sufficient leverage to remove the magnets from the plug part 30.

At least one pogo pin 15 is assembled through a window 16 of the case 10. The at least one pogo pin 15 relays signals to a connector pattern 26 on the PCB 25. Pogo pins are used because they include a spring which maintains a stable connection during relative movement between the at least one pogo pin 15 and connector pattern 26. The at least one pogo pin 15 may be assembled in many combination through a custom molded case.

Case 10 includes vertical groove 11, horizontal groove 12, window 16, and alignment pins 17. Grooves 11, 12 in conjunction with ridges 21, 22 provide latching functionality to the magnetic connector 60. Latching of the vertical groove 11 to the vertical ridge 21 prevents horizontal movement between the connectors which could introduce noise into the system. Similarly, latching between the horizontal groove 12 and horizontal ridge 22 prevent vertical movement between the connectors, which could also introduce noise into the system.

Window 16 accommodates the at least one pogo pin 15 to relay signals to the connector pattern 26. Window 16 can be merged to the case 10 along with the at least one pogo pin 15 by custom molded case 10.

Alignment pins 17 provide mounting and alignment functionality when the case 10 is mounted on a surface.

The receptacle part 40 of the magnetic connector 60 includes case 20, magnets 23 and 24, printed circuit board (PCB) 25, connector pattern 26, ridges 21 and 22, and alignment pins 27.

Magnets 13, 24 and 14, 23 are assembled with opposite polarities facing each other respectively, at the connected state. This provides self-aligning functionality as the plug part 30 and receptacle part 40 will repel each other if they are misaligned when a user attempts to connect them. Magnets 23, 24 on the receptacle part 40 are replaceable in the event they lose their magnetic force due to prolonged use. The magnetic connector 60 can provide sufficient leverage to remove the magnets from the receptacle part 40.

Printed circuit board (PCB) 25 and connector pattern 26 are used to establish an electrical connection to the at least one pogo pin 15. The connector pattern 26, on the PCB, is surface treated to prevent deformities and abrasion caused by physical and mechanical contact with the at least one pogo pin.

Case 20 includes vertical ridge 21, horizontal ridge 22 and alignment pins 27. As noted above ridges 21, 22 and grooves 11, 12 provide latching functionality when the plug part 30 and the receptacle part 40 of the magnetic connector 60 are connected. As noted above, latching the vertical ridge 21 to the vertical groove 11 prevents horizontal movement between the connectors which introduces noises. Similarly, latching between the horizontal ridge 22 and horizontal groove 12 prevent vertical movement between the plug part 30 and receptacle part 40 of magnetic connector 60. The alignment pins 27 provide mounting and alignment functionality when the case 20 is mounted on a surface.

As shown in FIG. 1 the electronics 5 for processing or transmitting signals are connected to fabric 1 by directly attaching the connectors 4, 6 together or through conductive wires 7. The electronics 5 may include amplifiers, microprocessors, memories to store data, transceivers, antennas and power management circuits and global positioning system (GPS) module.

The amplifiers in the electronics amplify the signals from the sensors for further signal processing in microprocessors. The amplified signals are transferred to the microprocessors for signal processing such as analog to digital conversion and arithmetic or logical calculation. The processed signals are stored in memory such as flash memories, SD cards, CF card, etc. The GPS module provides current location data. The transceivers transmit the data to the remote server or external computing equipment wirelessly or with a wire. The wireless communication with the transceivers between the electronics and the remote server or the external computing equipment can be established by standard communication protocols, such as Bluetooth, Wi-Fi, ZigBee, infrared data association (IrDA), near field communication (NFC), ultra-wide band (UWB), WiMAX, and Mobile communication or non-standard customized protocols.

The antennas for wireless communication may be a surface mount (SMD) type, PCB antennas printed on the substrate, mechanical type antennas, or printed on the garments. The antennas can have multi-resonance frequencies with such as fractal structures to accommodate several wireless communication standards such as Wi-Fi (2.4 GHz/5.8 GHz), NEC (13.56 MHz), Bluetooth (2.4 GHz), ZigBee (2.4 GHz), WiMAX (2.5 GHz, 3.5 GHz) and mobile communication (800 MHz, 850 MHz, 1.7 GHz, 1.9 GHz, 2.1 GHz, 2.5 GHz).

Figure 3:
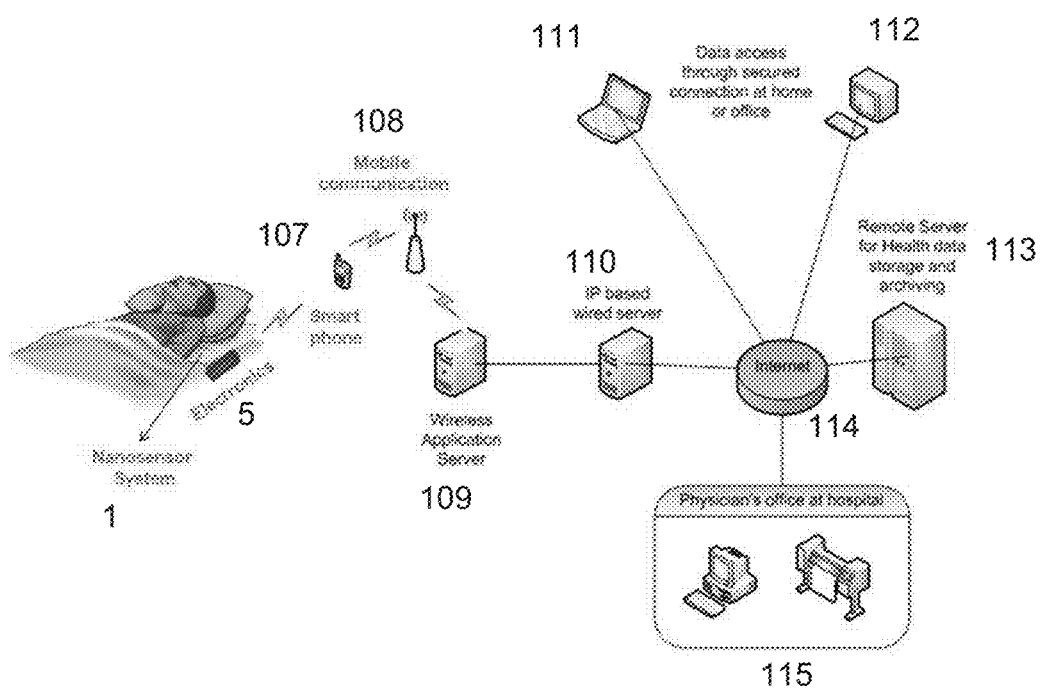
FIG. 3 shows a diagram of a nanosensor system connected to a cloud service.

The electronics 5 can transfer data to smart phones with a software system, that can collect sensor data over Bluetooth and relay data over 2/3/4G, Wi-Fi, WiMAX, an outgoing RFID connection or via cloud services. FIG. 3 shows the example of nanosensor system 1 on bed sheet in connection with a cloud network. The nanosensor system 1 is connected to electronics 5 which transmit data to smart phone 107. The data from smartphone 107 sends data over a cellular phone network via mobile communication system 108, which in turn is in communication with wireless application server 109. IP based wire server 110 communicates the data over the internet 114 with remote server for health data storage and archiving 113, the patient or caregiver's laptops 111 or desktops 112, and physician's office or hospital computer systems 115.

The software system provides two other distinguishing features. First, it implements filtering algorithms on the cell phones 107 to mitigate issues due to motion and other artefacts, rendering clean data. It provides a visualization interface at the cell phone 107 through which users can see salient features of pathophysiological signals. Second, it tags the data with the location of the user. The location (latitude, longitude) collected is key for both backend services (113, 115) and the user himself/herself (111, 112, 107) in case of a medical emergency. The software on the phone 107 runs simple machine learning algorithms to perform preliminary anomaly detection. Alternatively, the machine learning algorithms can be performed on electronics 5, or on a remote server such as server 113. In case of an emergency, the phone 107 can either alert the user and recommend him/her to hospital locations near his/her present location or make an automated call to the patient's physician (115) with his/her present location. Thus caregivers can access vital information anywhere and at any time within healthcare networks for global level active monitoring.

Current location data from a Global Positioning System (GPS) module is included in the nanosensor system 1, in the electronics 5, or the phone 107. The GPS location is tagged to the user's data then transferred to the cloud network and stored in a secure database 113 (an SD card can also be installed in the cell phone 107 or electronics 5 to save the data). For physician diagnostics a new backend service is provided, where the doctor can log into secured data base 113 and can visually look at the past and current pathophysiological data (as necessary). If the physician desires, he/she can use the machine learning algorithms to detect abnormalities in the data, the VOW service can make phone calls or send SMS messages to physicians. Additionally, the mobile device 107 can send relevant abnormal data in advance to emergency services. The mobile device 107, if equipped with a camera, can prompt the user to start a video call. These processes and steps are described in FIGS. 4 and 5.

Figure 4:
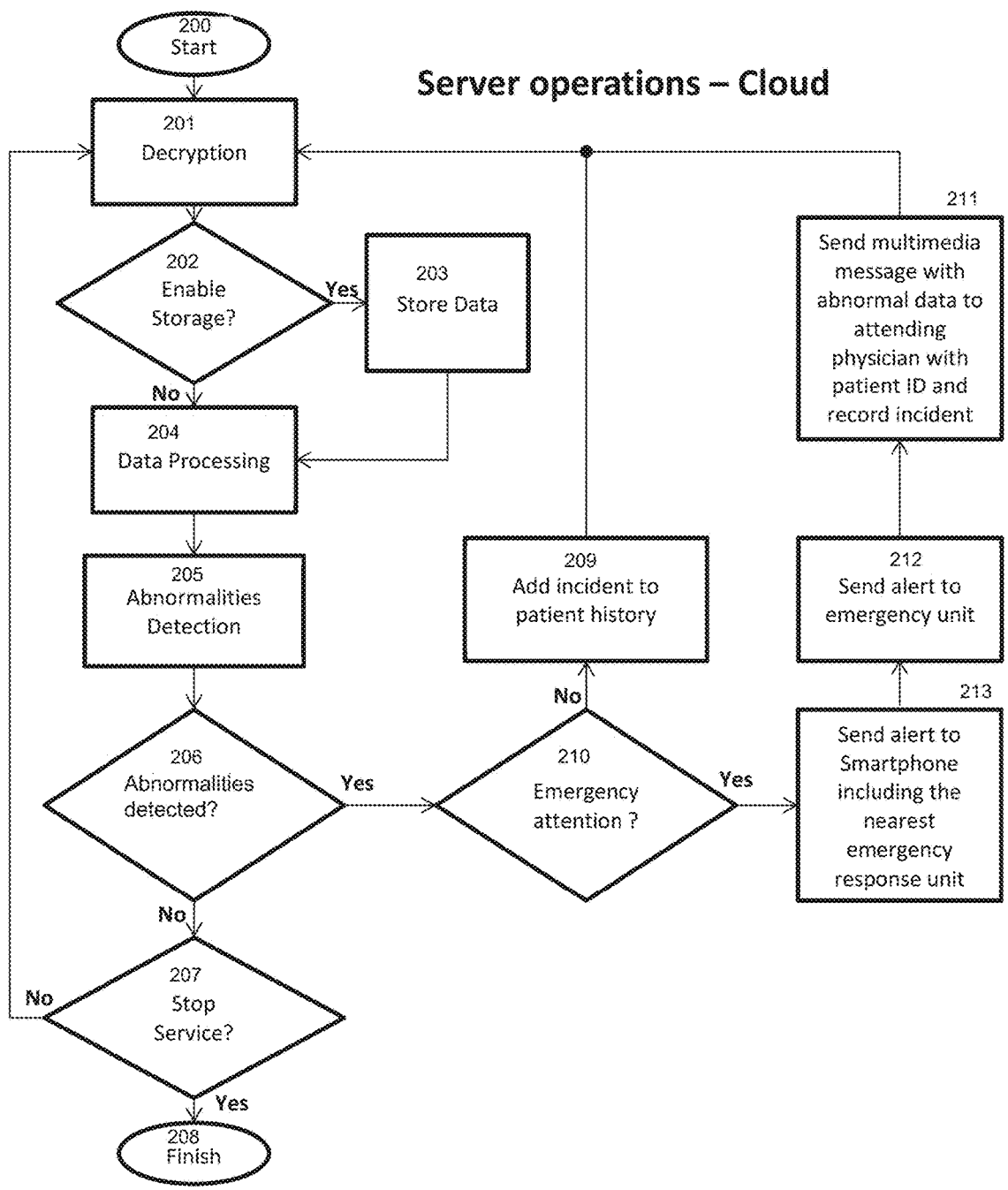
FIG. 4 shows a flowchart of an emergency response protocol implemented on a cloud service.

FIG. 4 shows the sequence of processes and steps followed by a cloud server when an emergency abnormal condition reflected by abnormal health data is detected. The steps are as follows, following step 200 (start):

1. Decryption—In step 201, the patient's data is received and decrypted. In this block data refers to patient's data which may include biopotential signals in an encrypted (maybe any form of encryption like HTTPS) digitized format like Electrocardiogram (ECG), Electroencephalogram (EEG), Electrooculogram (EOG) and Electromyogram (EMG). This data is received and decrypted. The data may also be optical plethysmography, acoustic data measuring heart activity or body impedance data, 2. Enable storage ?(Yes/No) In step 202, the process determines if storage of the data is enabled. In this regard, if the patient is a subscribed user of the cloud storage services, storage is enabled (Y), and the incoming patient data is stored (step 203)

3. Data Processing (Step 204): In step 204, the decrypted data is processed. In particular, the system appends data to a corresponding patient's records with GPS location and time. The process of appending data can involve the integration of the cloud services with exiting electronic health records data on another server. The appending of data will be performed by matching the current test that is acquiring the patient data with a unique identifier in the electronics health data records. Alternatively, in the absence of an electronics health records management system, the data can be tagged and matched to an hospital or a healthcare data provider's system for unique identification of patients and the tests that they were prescribed. The database architecture for hosting the patient's data is secure and maybe a relational database, SQL database or NoSQL or NewSQL database.

4. Data processing (Step 204)—The step of data processing 204 further includes processing the patient data to extract features which are considered representative of a specific state of the patient's health. These features are of a nature that can be used to distinguish the patient data from a normal individual from a patient with pathological conditions. The selection of the appropriate feature set maybe done through machine learning algorithms, multidimensional pattern space embedding or other known feature selection algorithms.

5. Abnormalities Detection—(Step 205) Based on the nature of the patient data e.g., whether it is a biopotential or other physical data like acoustic or optical) and the region where the data is collected, a representative feature set is derived from the data and checked against a known database of pathological data. The differentiation of these features will be used to determine abnormal or pathological data in step 205. The abnormalities may be indicative of pathological cardiac rhythm or pathological neural activity of the brain associated with neurological disorders like Epilepsy.

6. Abnormalities detected? (Step 206) This step makes the decision on whether an abnormality was detected based on the features that were extracted previously and compared to a database of previously known abnormal feature sets.

7. Stop Service? (Yes/No) (Step 207) This step determines whether the stipulated duration of service when the patient data is previously prescribed to be collected, has expired.

8. Emergency attention? (Yes/No) (Step 210) This step determines if the pathological condition determined by the feature classification methodologies (steps 204-206) is a severe kind which puts the patient at a high risk or a non-critical low risk abnormality.

9. Add incident to patient history (Step 209). If the abnormality was determined to be non-critical, no notifications are sent to the patient or the physician at a hospital. The detection is recorded as part of the patient's test data and entered into their electronic health record.

10. Send alert to Smartphone including the nearest emergency response unit. (Step 213) If the abnormality was determined to be critical, the server sends a message to the smartphone in the form of an SMS, a packet over the HTTPS, XML or JSON. The content of this message include the contact information of the nearest emergency or urgent care unit based on the current GPS location of the phone. The mobile application running on the smartphone can perform this operation or it can send the server the current GPS location and the server can then respond with the contact information.

11. Send alert to emergency unit—(Step 212) The emergency or urgent care facility identified in the previous step is also notified through a voice call. SMS, MMS or through a packet over the HTTPS, XML or JSON to a local server to provide the urgent care staff with the information about the patient and the preliminary diagnostic data available.

12. Send multimedia message with abnormal data to attending physician with patient ID and record incident in patient's history (Step 211)—The multimedia message sent in step 211 may consist of all the data associated with the detected abnormality. This message may include data before and after the detected abnormality. This message may include a multitude of data modalities like biopotential, plethymography and acoustic data.

Figure 5:
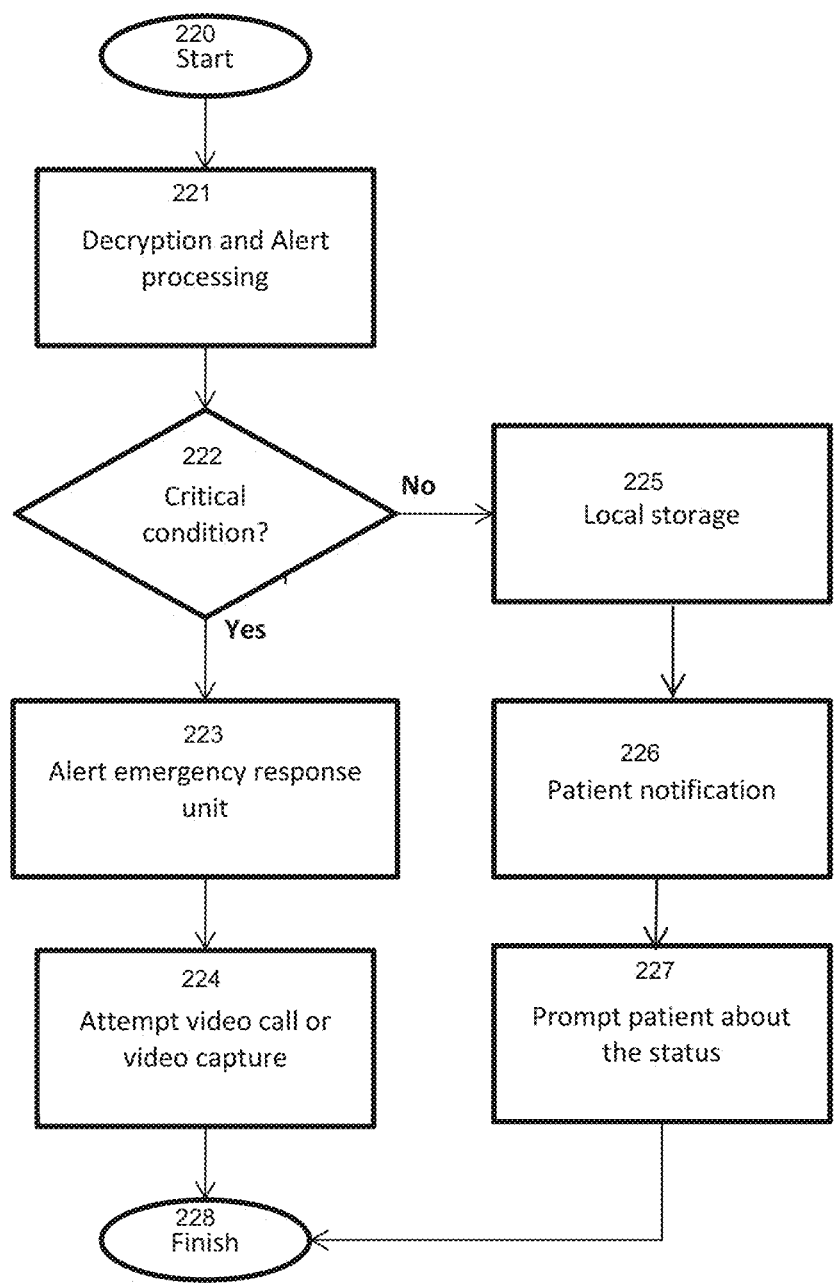
FIG. 5 shows a flowchart of an emergency response protocol on a mobile device.

FIG. 5 shows the sequence of processes and steps followed on a mobile device in response to an emergency message sent by a cloud server. The steps are as follows after start 220:

(1) Decryption and Alert Processing (Step 221). In this step, the smartphone application receives a SMS, MMS or a packet over HTTPS, XML or JSON from the cloud server. This packet is encrypted to protect patient heath data. Accordingly, in this step the data is decrypted;

(2) Critical Condition? (Yes/No) (Step 222). In this step, the mobile application determines whether the message received from the server indicates a critical abnormality;

(3) Alert emergency response unit—(Step 223). In this step, if the message was determined to indicate a critical abnormality, the mobile application can place a voice call, SMS, MMS or through a packet over the HTTPS, XML or JSON communicate to the nearest emergency or urgent-care center that the patient is in critical condition;

(4) Attempt video call or video capture. (Step 224). In this step, the patient can be prompted by the mobile application to start a video call with the emergency response team. This can be a notification on the smartphone or an automatically enabled feature supported by the smartphone;

(5) Local Storage—(Step 225) In this step, if the abnormality detected was determined to be non-critical, the smartphone application records the event locally in its storage and retains it as application related data;

(6) Patient Notification—(Step 226). In this step, the mobile application also displays an alert message to indicate to the patient that a non-critical anomaly was detected;

(7) Prompt patient about the status—(Step 227). In this step, the smartphone application after having notified the patient that a non-critical anomaly was detected, prompts the patient to setup an appointment with his/her physician.

Figure 7A:
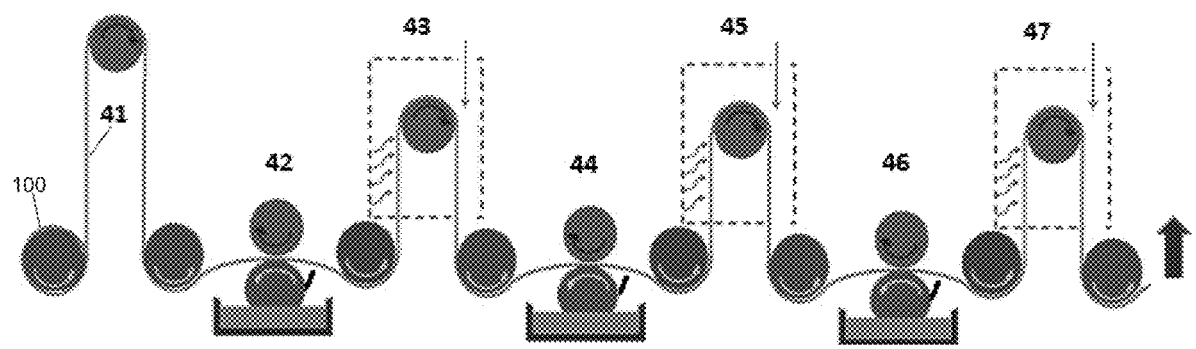
FIG. 7A shows a diagram of a first portion of a roll to roll gravure printing process for conductive tracks.
Figure 7B:
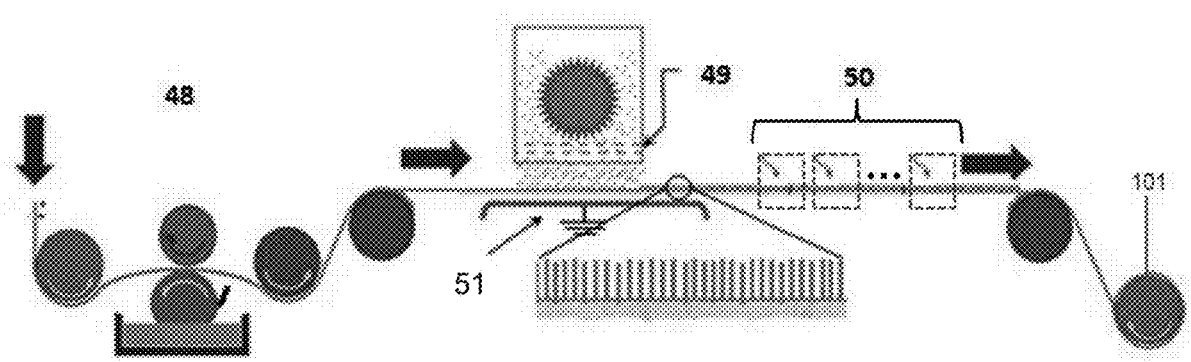
FIG. 7B shows a diagram of a second portion of a roll to roll gravure printing process for nanosensors.

FIG. 7A-B shows a Roll to Roll gravure printing process which prints conductive tracks printed on a fabric web 41 with a gravure printing machine such as a Taejin Roto Gravure Printing Machine. A web 41 of fabric is fed to the press from a fabric roll 100, and the printed fabric exiting the press is wound into a printed fabric roll 101. In the press, a base insulation layer is applied to the web 41 with gravure print head 42 and is thereafter dried in a dryer 43. A conductive layer is selectively applied to the web 41 with a gravure printing head 44 and thereafter dried in a dryer 45, to provide the conductive tracks 3. An insulative cover layer is selectively applied to the web 41 with a gravure printing head 46 and thereafter dried in dryer 47 to cover the conductive tracks while leaving the conductor exposed for later placement of sensors 2. This is followed by printing of a conductive or non-conductive adhesive layer onto the web 41 in gravure printing head 48 as discussed below with regard to FIG. 7B. The printing head 48 applies the adhesive to the location on the fabric web 41 onto which the nanostructured fibers are to be applied by electrostatic/pneumatic deposition unit 49 and then subsequently dried in dryer 50, either by thermal or photonic sintering. If the nanostructured fibers are precoated with conductive film prior to deposition, then the adhesive used is preferably conductive adhesive. If the nanostructured fibers are coated after deposition, then non-conductive adhesive can be used because the adhesive can be coated with a conductive material along with the coating of the nanostructured fibers.

Each of the gravure print heads (42, 44, 46, 48) includes a patterned drum, a doctor blade, an ink vat, and a roller that presses the fabric against the patterned drum. Tensioning rollers are shown either side of the patterned drum (representing a set of tensioning rollers), and a drying assembly (43, 45, 47) is also shown. The patterned drum only fractionally dips into the ink vat to pick up viscous ink on its surface. The surface of the drum gets scrapped off by a doctor blade to leave only the ink that is within the patterned groves on the drum. This ink is transferred on to the fabric to form the intended pattern.

The dryers 43,45,47,50 each include a drying assembly that consists of a heating element that brings up the temperature of fabric to curing temperature of the ink and a convective cooling assembly cools down the fabric sufficiently to print the next layer.

FIG. 7B illustrates the process for deposition of nanostructured fibers on fabric, which can have conductive inlays printed from the process described in FIG. 7A. The print head 48 prints an adhesive layer at the locations on the fabric onto which the nanostructured fibers are to be applied. The adhesive is conductive in areas in which an electrical connection for nanosensors to the conductive inlay is desired. In electrostatic/pneumatic deposition unit 49, the nanostructured fibers get driven towards the substrate by electrostatic field/pneumatic force and attached to the adhesive layer in vertically upright position. The deposition unit 49 is an enclosed machine with fabric rolling in from one end and rolling out from the other end, such as Maag flocking machine for flat surface, that contains electrostatic charged nanostructured fiber that are deposited by electrostatic field/pneumatic force. After curing and cooling in dryer 50, the nanosensor fabric gets rolled on to a fabric roll. In this embodiment, the nanostructured fibers are precoated prior to deposition by the flocking machine in the manner discussed above.

A challenge in processing is that nano-fibers by themselves cannot penetrate the meniscus of the adhesive on the substrate during a standard electrostatic deposition process (flocking). Also, such small structures are very difficult to handle during deposition and require a closed chamber or vacuum. To solve this problem, two or three component yarn, with polymer nanofibers embedded in a matrix of another polymer, can be used for textile fabrication followed by dissolving of the matrix polymer to expose the nanofibers. The fibers can be cut and flocked like normal micrometer scale (micro-denier) fibers and a subsequent dissolving step can release the nanofibers, resulting in vertically free standing nanostructures on the textile. Composite fibers are best suited because they can be flocked as micro-denier fibers and then bundled polymer nanofibers can be released by dissolving the matrix polymer.

Figure 6A:
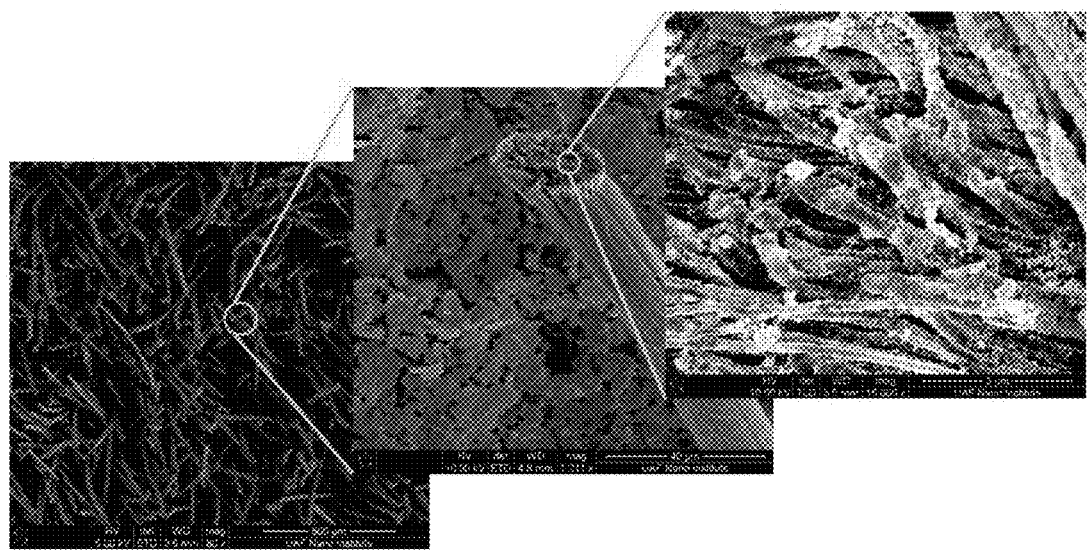
FIG. 6A shows cross-sectional views of polymer fibers distributed in a matrix of another polymer.

FIG. 6A shows a cross-section of bicomponent fiber at 80×, 1211×, and 1500× magnification, where higher magnifications show the nanofibers exposed after dissolving the matrix polymer. FIG. 6A shows that 400 fibers of one polymer fibers are distributed in a matrix of another polymer. Given the micro-denier dimension of fibers, a bundle of as much as 1500 nanofilaments can be accommodated. Composite fibers are deposited as microfibers and then bundled polymer nanofibers can be released by dissolving the matrix polymer. This is followed by metallization of the structures with silver by an electroless plating method.

A three dimensional helical structure 61 can be achieved by extrusion of composite fiber, where the constituent fibers shrink at different rates upon crystallization. The shrink rate is governed by variation in molecular cross-linking of the polymers.

The composite fibers can be cut in to small length of 500 μm to 1.5 mm using a cryo-blade, cooled down to −20° C. to −40° C. to get clean cut with no sticky ends.

Figure 6B:
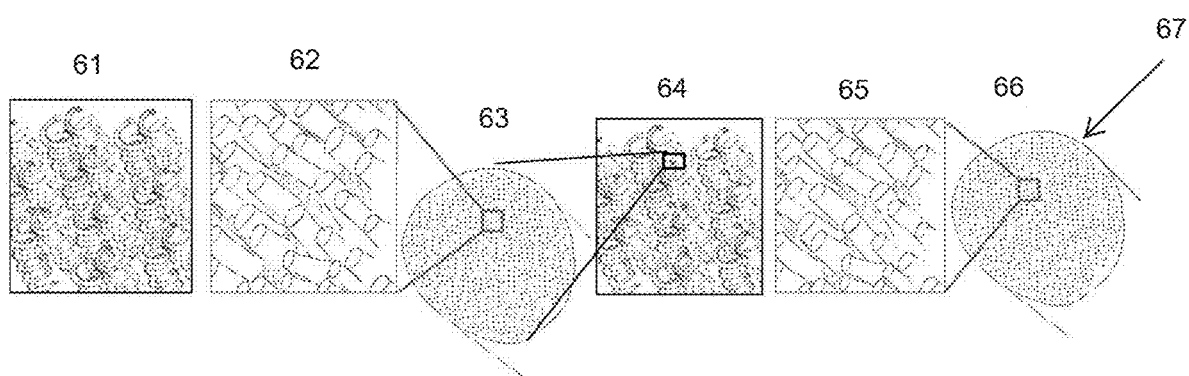
FIG. 6B shows plain views of textile based nanostructures.

FIG. 6B shows a composite fiber 67 which is formed from combination of two or three polymers, that are mutually immiscible. The polymers can be drawn in to yarn by extrusion and cut into fibers so that a fractal architecture can be formed after dissolving the matrix polymer(s), which is one polymer forming long fibers (61 or 62) in a matrix of the other polymer 63 optionally forming long fiber bundles (64 or 65, respectively) in a matrix of a third polymer fiber 66. A cross-section of such a fiber shows that 60 to 1500 nanometer fibers of one polymer are distributed in matrix of the other polymer, thus giving the impression of islands in sea. FIG. 6B further shows that the combination of two or three polymers, that are mutually immiscible, can be drawn in to fibers by extrusion as fibers within fibers within fibers.

A variant of this combination is shown in FIGS. 6A-B, where the matrix polymer encompasses the inner fiber bundles and then extend further. Many such cut fiber can be deposited on the surface of a fabric to form free standing nanostructures.

The free standing nanostructured fibers can be coated with film of conductive material such as silver, gold, platinum, polyaniline, polypyrrole, poly(3,4-ethylenedioxythiophene) to make them electroactive for applications such as but not limited to health monitoring EKG, EEG, EOG, EMG electrode application, touch sensors. They can be coated with metal oxide such as films for capacitive sensing application such as but not limited to respiration rate, air quality, gas sensing, and water quality. They can be coated with piezoelectric material film like polyvinylidene difluoride (PVDF) for application such as but not limited to motion sensing, acoustic transduction, noise dampening, impact sensing.

Synthetic long chain polymers such as Polyester, Nylon, Polypropylene, Polybutylene, Polylactic acid, Poly-acrylonitrile, Polycarbonate, Polyurethane, Polyolefin, Polyimide and. Polyaramid can be melt blown or solution blown, or extruded and spun into fibers on spinneret. Exemplary spinnerets are described, for example, in U.S. Pat. Nos. 4,406,850, 5,162,074, and 5,851,562, the entire disclosures of which is incorporated herein by reference. The extrusion template for drawing out the fibers can be modified to obtain fibers with diameter in the order of nanometers (10-2000 nm). These processes can obtain fibers that are only as wide as the single layer crystal made of polymer chains. The conventional synthetic polymer fiber spinning technology can be improved to produce composite fiber. Spinneret design can be modified to make groups of nanometer scale holes in nano or mesoscaled shafts distributed within the injection nozzle of micro-denier yarn. The diameter and length of nanometer holes and shafts can be varied depending on the melting temperature, glass transition temperature and molecular weight of the component polymers, This is done to achieve well-defined fractal architecture of two/three polymer components in a micro-denier yarn.

For the two/three component yarn, a multicomponent extruder fed spinning unit can be used where two/three extruders feed the required two/three polymers in molten form to a spinneret with a special configuration to provide the filaments of one or more polymers of 10-100 nanometer dimensions in a matrix of the other polymer forming a micro denier yarn. The yarn can be multi polymer component bundles consisting up to 1000-1500 entities dispersed in the matrix. The nanometer scale filaments can be formed by polymers such as Polyesters such as Polyethylene terephthalate (PET), Polyethylene naphthalate (PEN), Polymethylene terephathalate (PMT), Polybutylene terephthalate (PBT), Polyurethanes both polyester and polyether based, Polyurethanes with IPN and semi-IPN structure, Polyamides such as Nylon 6, Nylon 6,6, Nylon 6,10, Polyolefins such as Polyethylene and Polypropylene, Polycarbonates, Polyacrylonitrile, Styrene copolymers. The matrix can be formed by polymers such as Polyethylene terephthalate modified with Sulfonated isocyanate, Polystyrene, Polyvinyl alcohol, Ethylene vinyl alcohol, Polyacrylamide, Poly Lactic acid.

Figure 10A:
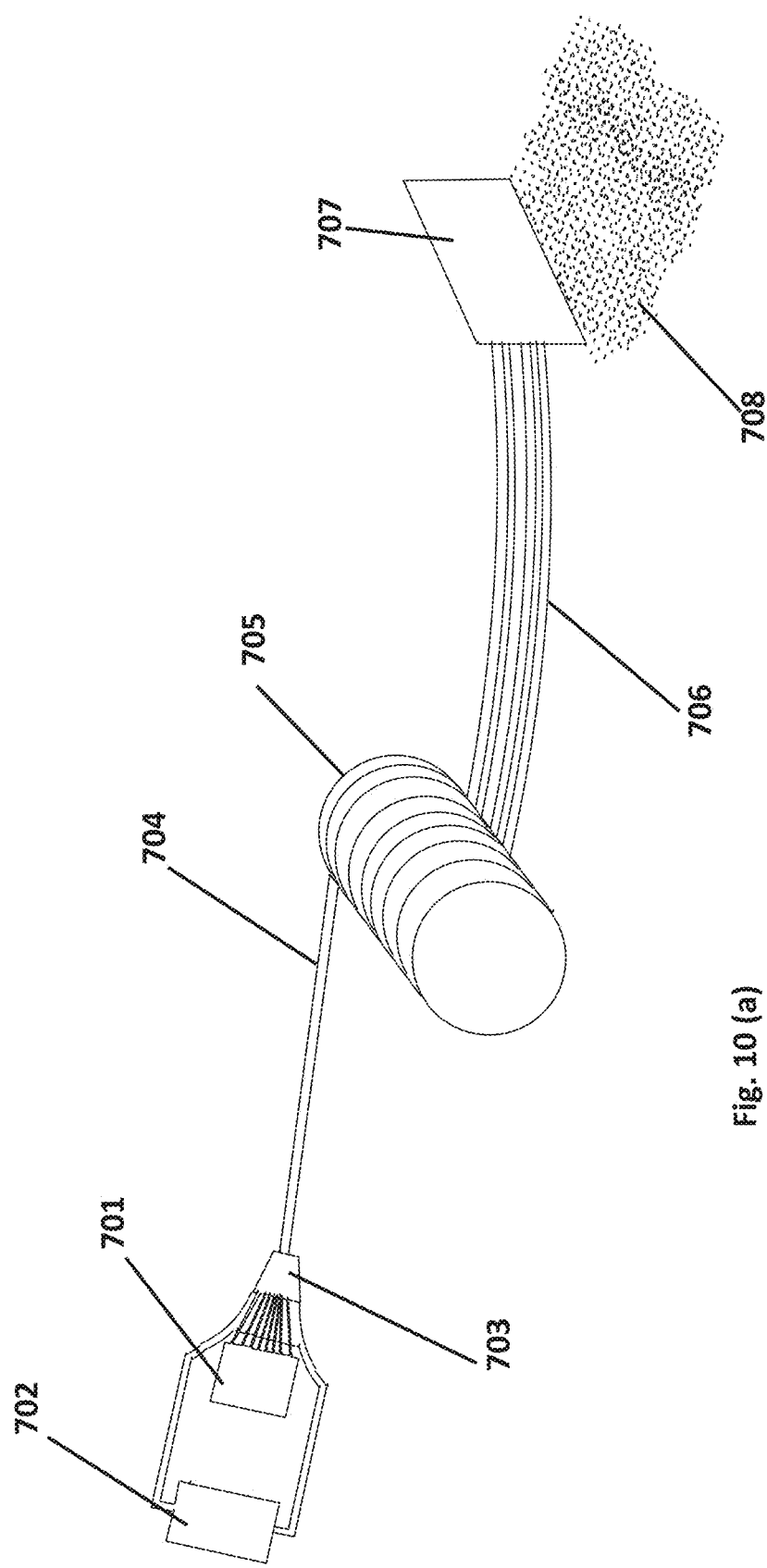
FIGS. 10(a) and (b) illustrate a process of forming two and three component nanostructured fibers.
Figure 10B:
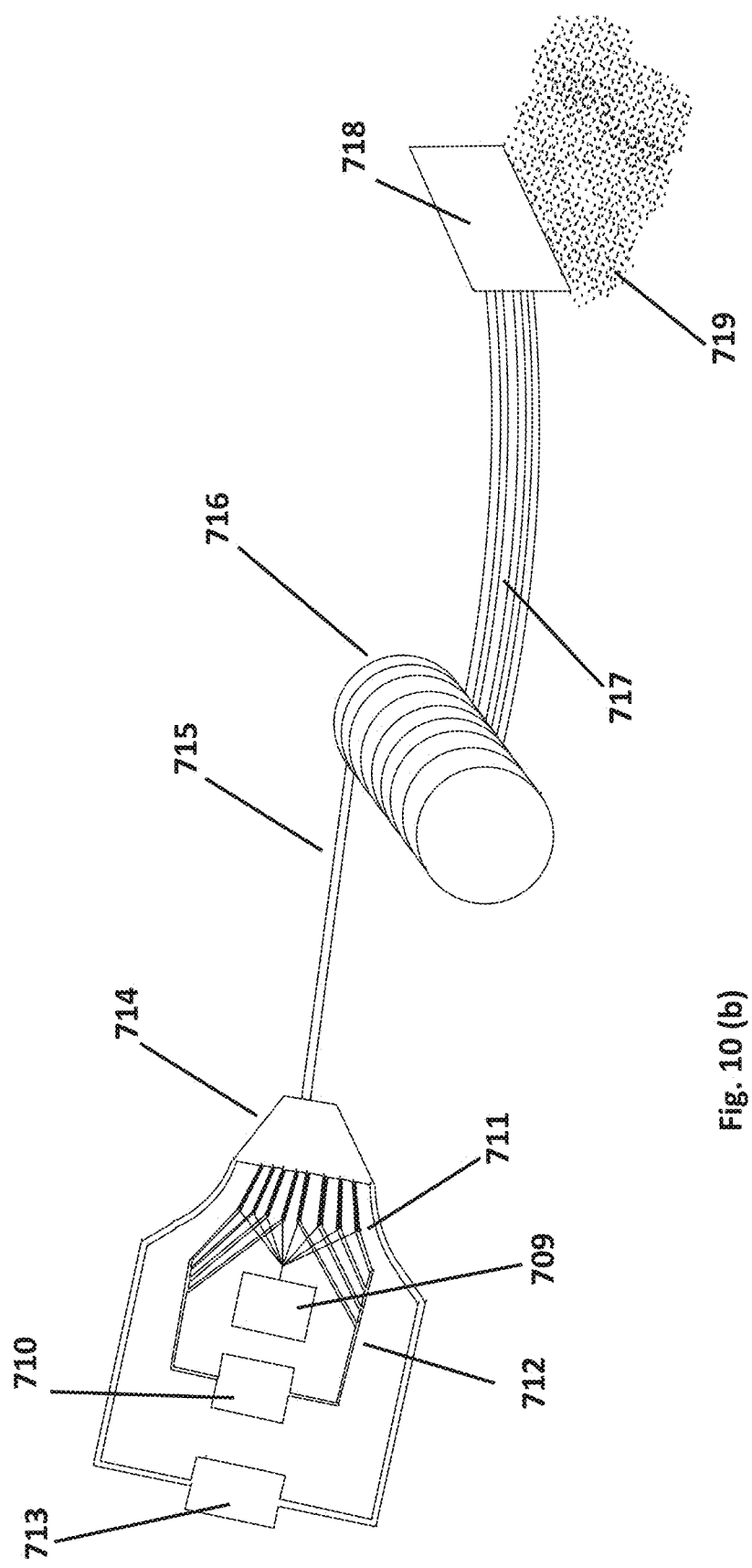

FIGS. 10(a) and (b) illustrate a process of forming two and three component nanostructured fibers, and FIGS. 11(a)-(f) illustrate spinnerets for the process of FIGS. 10(a) and 10(b) which are configured to have groups of nanometer scale holes in mesoscaled shafts with the injection nozzle.

FIG. 10(a) illustrates how composite fibers 708 are formed from a combination of two polymers 701, 702 that are mutually immiscible. FIG. 10(b) illustrates how composite fibers 719 are formed from a combination of three polymers 709, 710, and 713. In FIG. 10(a), the matrix polymer is polymer 701, and in FIG. 10(b) the matrix polymers are polymers 709 and 713. The polymers are combined via spinnerets 703 and 714 into two or three component composite yarn 704, 715. The composite yarn 704, 715 is wound into a roll 705, 716. The yarn is later unrolled and cut into fibers 708, 719 by a cryoblade 707, 718.

Referring to FIG. 10(a), two polymers in molten form are fed through respective extruders. In particular, a first polymer 701 and a second polymer 702 are fed separately into a spinneret 703 in molten form to produce a composite yarn 704. The ratio of the polymers is dependent on the density of the nanofilaments within the fiber. For example, if there are 1500 filaments of 200 nanometer diameter each with in a fiber of 20 micrometer diameter, then the volumetric ratio would be about 1:5.7 (nanofilament polymer 701: matrix polymer 710). Exemplary ratios could, for example, be from about 1:3 to about 1:10, preferably from about 1:4 to about 1:6. Ratios in excess of about 1:10 are also possible.

Figure 11A:
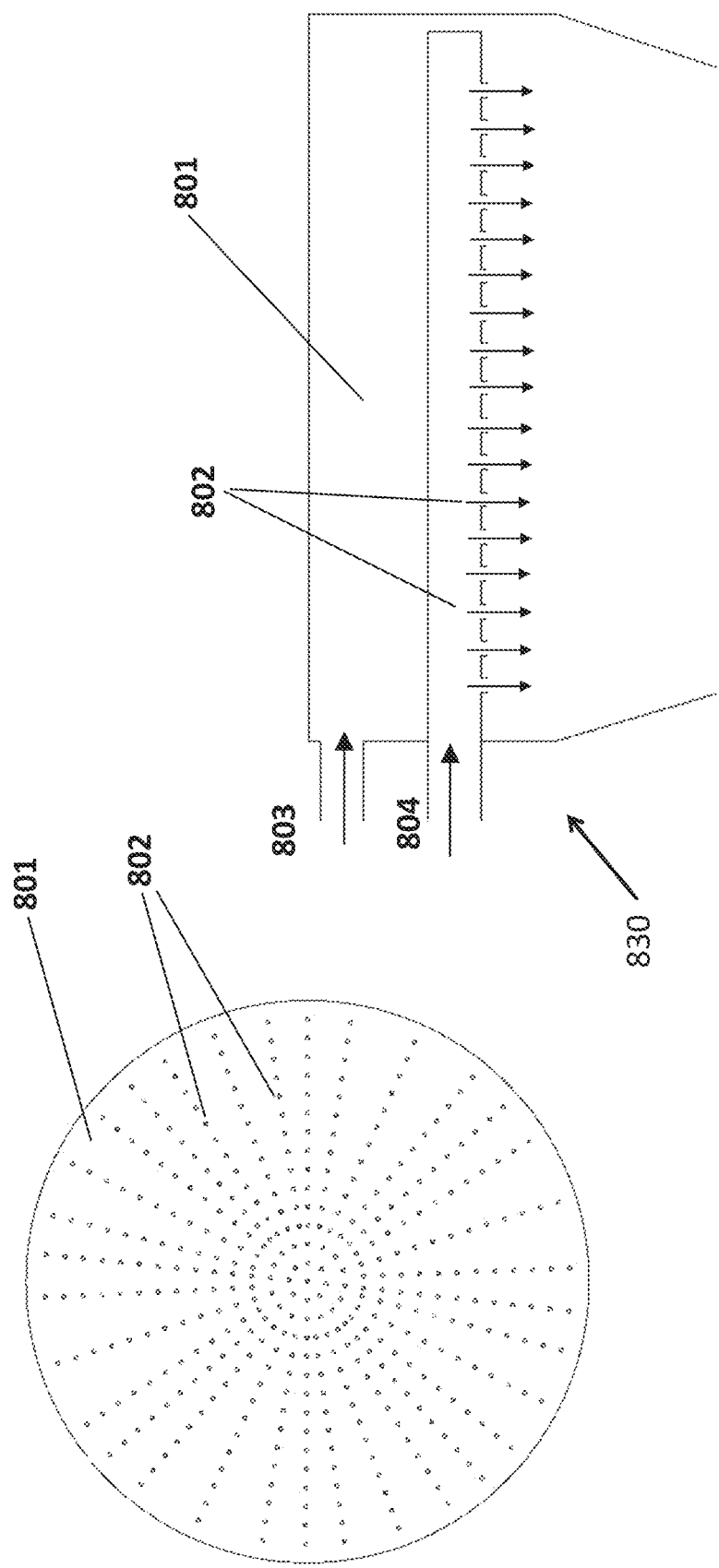
Figure 11B:
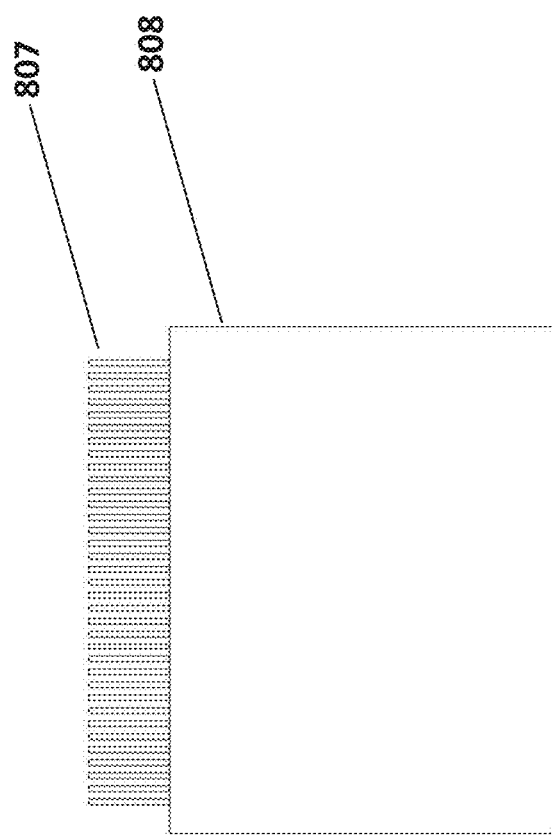
Figure 11B:
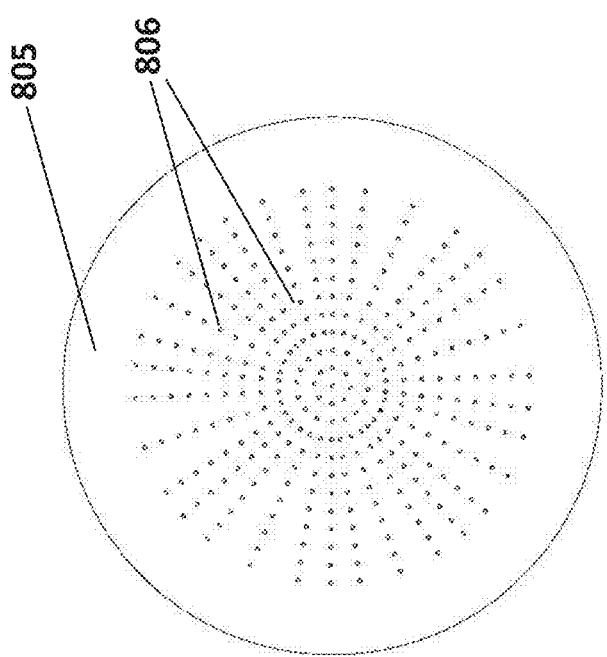
Figure 11C:
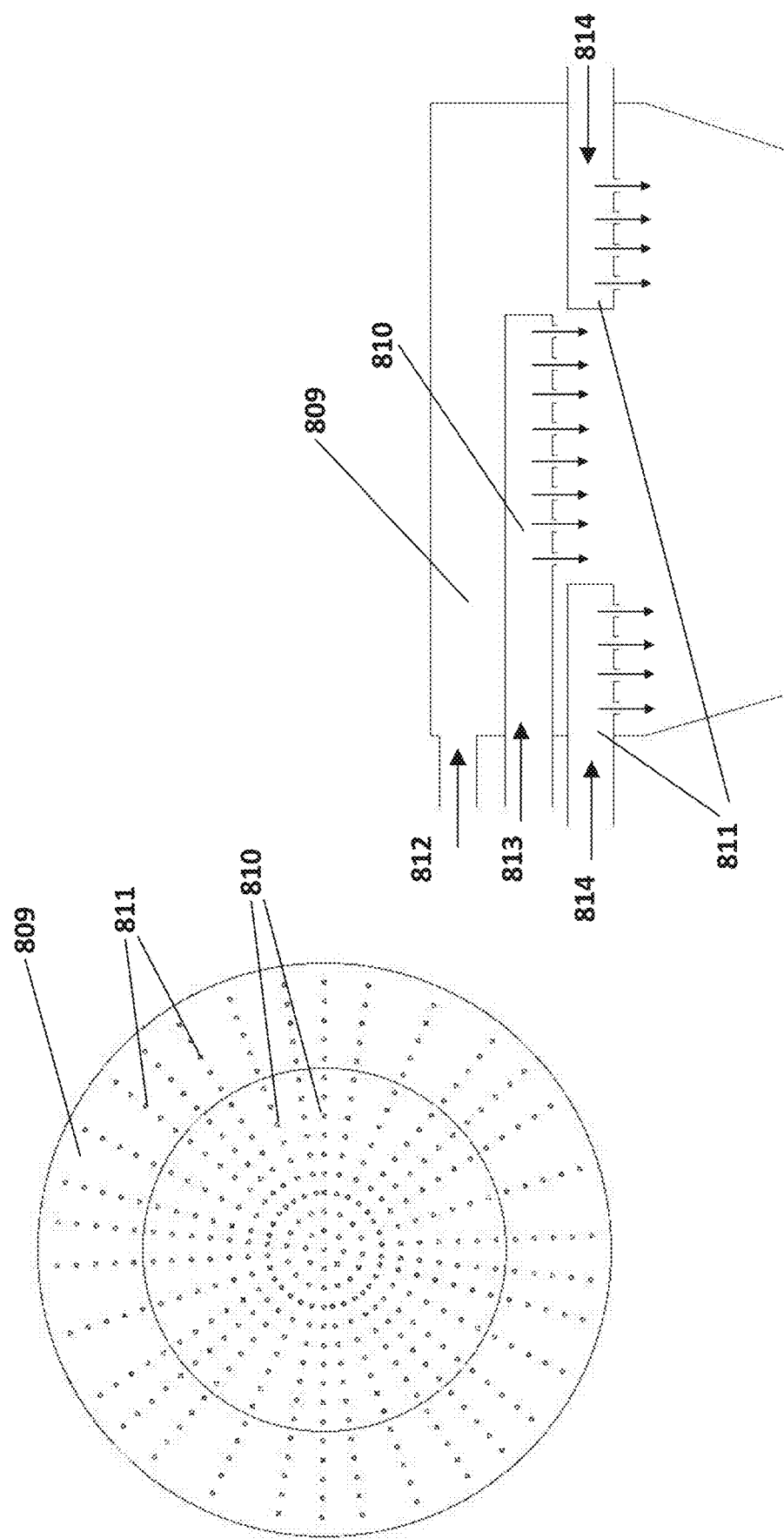
Figure 11D:
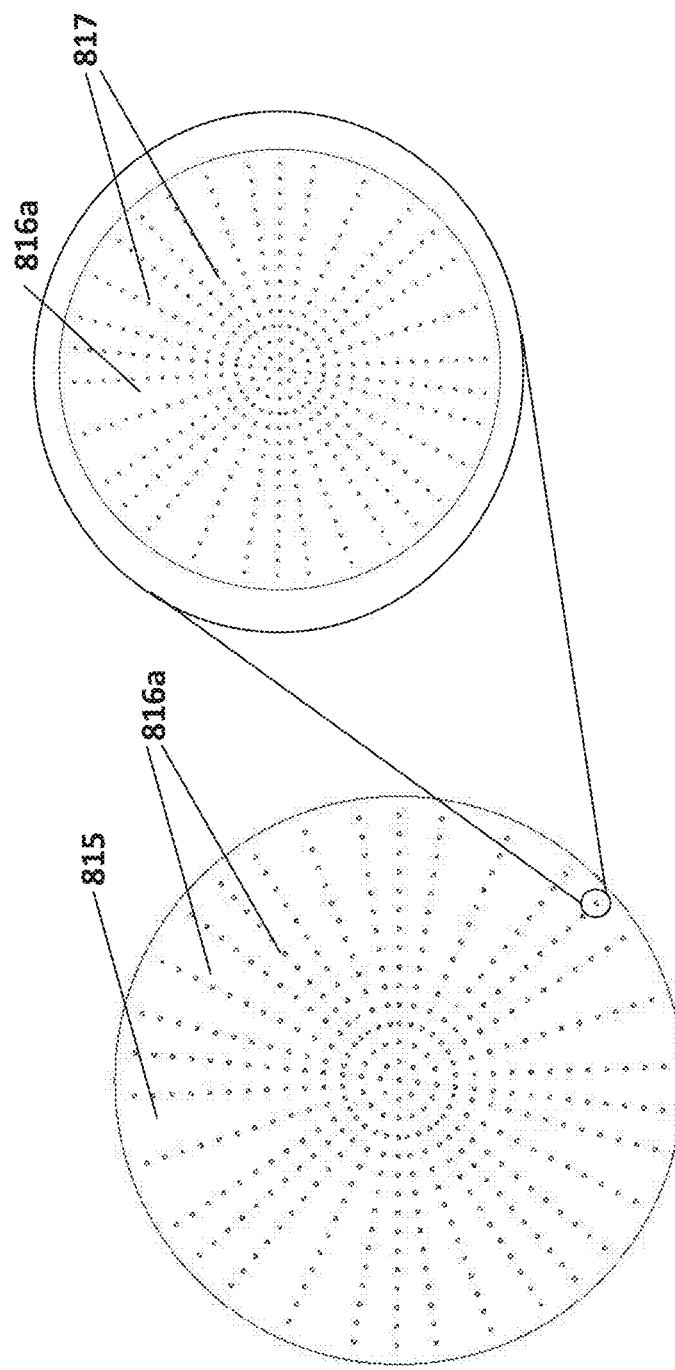

The spinneret 703 is configured to have groups of nanometer scale holes in mesoscaled shafts with the injection nozzle. FIG. 11(a) illustrates the spinneret 703 in further detail, and in particular, the groups of nanometer scale (200 nm or less) holes in mesoscaled (30 microns or less) shaft(s) within the injection nozzle 830. The nanometer scale holes 802 are provided on surface of conduit(s) 802 (one if which is illustrated for ease of depiction) that run across the mesoscaled shaft 801. In this regard a single mesoscale shaft 801 typically has multiple conduits 802. One such mesoscaled shaft gives one microdenier fiber with multiple embedded nanofilaments. A spinneret can have a plurality of such mesoscale shafts. The polymer 702 is fed into inlet 803 of conduit 801 and the polymer 701 is fed into the inlet 804 of conduit 802. The spinneret 703 combines or draws mutually immiscible polymers 701, 702 into two component composite yarn 704. The composite yarn 704 is then wound into a roll. The wound yarn 704 is then bundled in the form of tow 706 and then cut into composite fibers 708 having a length of about 500 μm to about 1.5 mm by a cryoblade 707. The cryoblade 707 cools the yarn down to −2.0° C. to −40° C. before cutting to get clean cut with no sticky ends. The result is composite fibers 708 which are comprised of one polymer forming long fibers 701 in a matrix of the other polymer 702. A cross-section of such a fiber would, for example, show 60 to 1500 nanometer fibers of one polymer distributed in matrix of the other polymer, thus giving the impression of islands in sea.

Returning to spinneret 703, the arrangement of nanoscale holes can be designed to achieve different distributions of nanofilaments within the stock of the composite fiber 708. For example, as illustrated in FIG. 11(*b*), the nanoscale holes 806 (which, as described in connection with FIG. 11(*a*), are provided on the surface of conduits that run across the mesoscaled shaft) can be concentrated in the center of the mesoscaled shaft 805 leaving a region of matrix polymer at the boundaries. Upon deposition (for example, in deposition unit 49) and matrix polymer dissolution of such fibers (for example, in an electroless plating process), the nanofilaments 807 can be exposed only at the tip of the composite fiber 708 while leaving a portion of polymer matrix stock 808 intact.

Similarly, as illustrated in FIG. 11(*c*) nanometer scale holes 810 at the center of the mesoscaled shaft 809 can be fed with one molten polymer mix and the nanoscaled holes 811 at the boundary of the mesoscaled shaft 809 can be fed with another molten polymer mix. The spinneret design can be modified to provide separate conduits 810, 811 for each molten polymer within the mesoscale shaft 809. Inlet 812 is provided for mesoscaled shaft 809, inlet 813 is provides for conduit 810, and inlets 814 are provided for conduits 811. Upon deposition and matrix polymer dissolution of such fibers, the nanofilaments of different chemical and mechanical properties can be obtained depending on the application.

Referring to FIG. 10(*b*), three polymers in molten form are fed through respective extruders. In particular, first polymer 709, a second polymer 710, and a third polymer 711 are separately fed into a spinneret 714 in molten form to produce a composite yarn 712. As compared with the two-polymer yarn of FIG. 9(*a*), the three-polymer yarn of FIG. 9(*b*) can be viewed as being comprised of the two-polymer yarn of FIG. 9(*a*) which is enveloped in a second matrix polymer 711. The ratio of the polymers is dependent on the density of the nanofilaments within the fiber. The ratio of could, for example, be from about 1:3 to about 1:10, preferably from about 1:4 to about 1:6 (polymer 710: polymer 713), and from about 1:2 to about 1:10, preferably from about 1:3 to about 1:5 (polymer 709: polymer 710). In both cases, ratios in excess of about 1:10 are also possible. The spinneret 714 is configured to have groups of nanometer scale holes in mesoscaled shafts with the injection nozzle.

The wound yarn 715 is then bundled in the form of tow 717 and then cut into composite fibers 719 having a length of about 500 μm to about 1.5 mm by a cryoblade 718. The cryoblade 718 cools the yarn down to −20° C. to −40° C. before cutting to get clean cut with no sticky ends.

The result is composite fibers 719 which are comprised of one polymer forming long fibers 709 in a matrix of the other polymer 710 which forms long fiber bundles 712 in a matrix of the third polymer fiber 713. A cross-section of such a fiber would, for example, show 10 to 1500 nanometer fibers of one polymer 709 distributed in matrix of another polymer 710 which together form bundles 712 in matrix of the third polymer fiber 713, thus giving the impression of islands in sea. There may be 60 to 1500 of such bundles within polymer 713.

FIGS. 11(*d*) through 11(*f*) illustrates the spinneret 714 in further detail. For the tri-component yarn of FIG. 10(*b*), the above mentioned nanometer scale holes shown in FIG. 11(*a*) are implemented as conduits 816 with nanometer scaled holes 816*a* projecting out of conduits 816, each conduit 816 having an inlet 819 as shown in FIG. 10(*d*)-(*e*). Smaller conduit(s) 817 each having an inlet 820 run within conduit 816. The conduit 817 has nanometer scaled tubes 817*a* projecting out of the conduit(s) 817 and into the nanometer scaled shafts(s) 816*a*, Also shown is mesoscaled shaft 815 with inlet 818.

FIG. 11(*f*) shows how the arrangement of FIG. 10(*d*) can be designed to achieve different distributions of nanofilaments within the stock of the composite fiber. For example, the nanometer holes and tubes 816*a*-817 can be arranged in concentric ring patterns with the number of holes/tubes increasing in successive outer rings in specific progression such as but not limited to Fibonacci series. Upon deposition and matrix polymer dissolution of such fibers, the nanofilaments 824, 826 get exposed and project outward in a spreading pattern (FIG. 11(*f*)) thus providing more effective surface area for contact at the fiber tips 825 and nanofilament tips 826.

Fibers 708, 719, with fibers in a matrix of another fiber (FIG. 10*a*) or fibers in a matrix of another fiber which in turn is in a matrix of another fiber (FIG. 10*b*), provide for the formation of a fractal architecture after dissolving the matrix polymer(s) 702, 710, 713 which is one polymer forming long fibers (701 or 709) in a matrix of the other polymer 702, 710 optionally forming long fiber bundles 712 in a matrix of a third polymer fiber 713.

The embedded nanometer size filament bundles in the encompassing polymer matric of the micro denier fiber are normally straight linear filaments. However these linear filaments can be converted into helical structure by using polymer components such as Polyesters such as Polyethylene terephthalate (PET), Polyethylene naphthalate (PEN), Polymethylene terephathalate (PMT), Polybutylene terephthalate (PBT), Polyurethanes with IPN and semi-IPN structure, Polyamides such as Nylon 6, Nylon 6,6, Nylon 6,10, Styrene copolymers as bi- and tri-component interpenetrating polymeric network (IPN) which are initially in form of helices by controlling the molecularly bonded hard segments such as poly-isocyanate and soft segments such as polyether based polyol of the polyurethane filaments. They can be converted into linear filaments and nanobundles during melt extrusion, by thermal and mechanical stress, through the spinneret to make the two/three component yarn. Subsequently, the filaments can be converted back to helical form by a thermal stimulus as required by the IPN, which are either embedded in the micro denier yarn or released as free standing nanostructures after dissolving the matrix polymer. The spinneret and the cooling zone can be modified for this helix based two/three component yarn.

Figure 8:
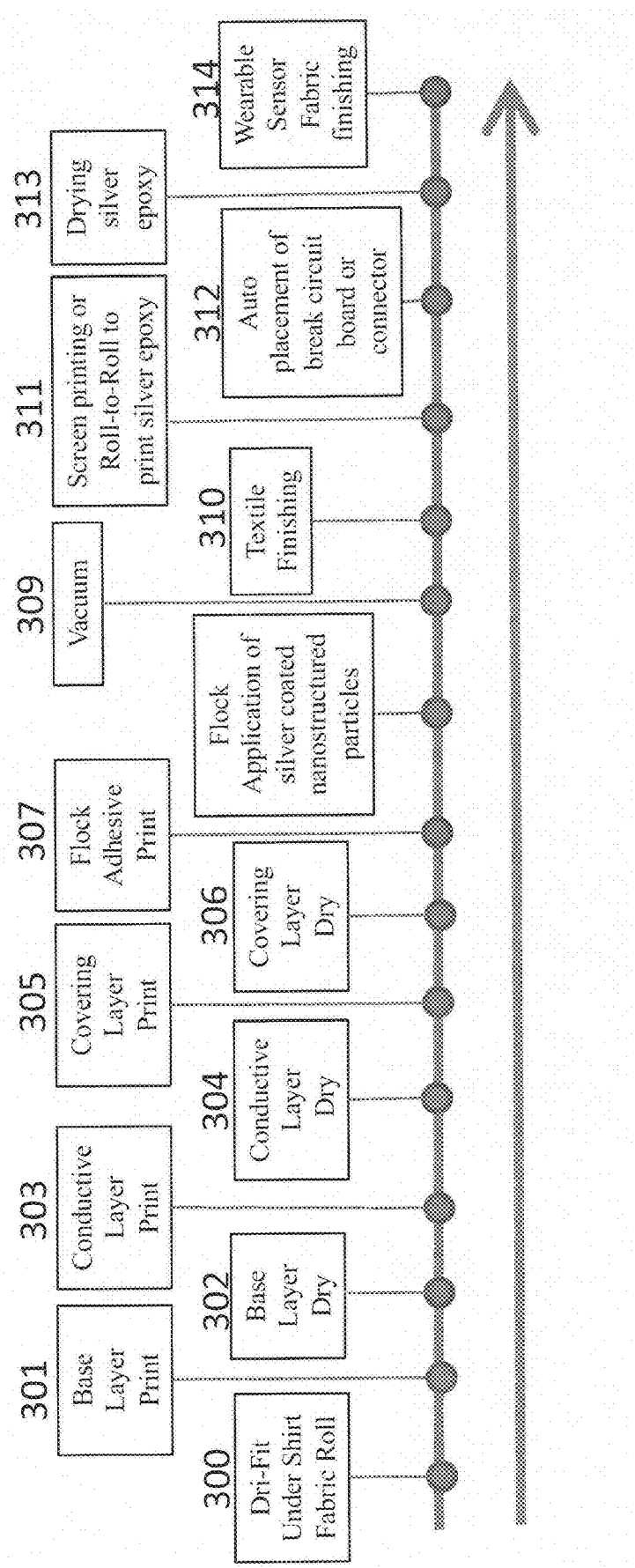
FIG. 8 shows a flowchart of a continuous roll-to-roll process for a fully integrated nanosensor system.

FIG. 8 shows the continuous roll-to-roll process for a fully integrated nanosensor system. The fabric roll is fed-in as the first input (Step 300). A first stage of the process is printing conductive tracks. The conductive tracks are sandwiched between two insulating layers to prevent interferences. Accordingly, the first stage of the process includes printing a base layer (step 301), drying the base layer (step 302), printing the conductive layer (step 303), drying the conductive layer (step 304), printing the cover layer (step 305) and drying the cover layer (step 306). A second stage of the process is printing sensors onto the fabric. The sensors are printed at precise sensor locations that are printed with flock adhesive. The silver coated nanostructured fibers are flocked on the fabric. Accordingly, the second stage of the process includes printing the adhesive layer (step 307), flock application of the silver coated nanostructured particles (step 308), vacuuming to remove loose particles (step 309) and textile finishing (step 310). Step 310 may, for example, include conformal coating of the nanosensor surface with dielectric polymer film such as poly 4-vinyl phenol. A third stage of the process is integrating the electronics and/or the connectors to the fabric by surface mounting and bonding. In this stage, a silver epoxy is screen printed or roll-to-roll printed on to the fabric((step 311), and the break out circuit board or connector (step 312), drying the silver epoxy to secure the circuit board/connector (step 313), and then fabric finishing (step 314). The fabric finishing step includes completed nanosensor system integration and/or fabrication of the form factor of wearable devices. The processes include cutting, sewing, lamination and/or fusing with another fabric or functional film(s).

In particular, the shirt fabric roll gets fed into the print head 42 for printing of base insulation layer ink and then in to the drying unit 43. The curing temperature, dependent on the printing ink, can range from 100° C. to 160° C. The fabric is then cooled down for the next print head. The conductive layer print step is performed by print head 44 which applies conductive ink for the electrical connectivity, and the conductive layer dry step is performed by dryer 45. The covering layer print step is performed by print head 46 which applies the covering insulation 46, and the covering layer dry step is performed by dryer 47, to complete the conductive inlay. The fabric then goes in to the flock application of silver coated nanostructures fibers step which is performed by printing head 48 (which applies the adhesive), deposition unit 48, and dryer 50, after which, the nanosensors are realized on the shirt fabric. In this embodiment, the nanostructured fibers are precoated prior to deposition by the flocking machine in the manner discussed above. Vacuum removes any un-attached nanostructured fibers from the fabric. Break circuit board or connector gets attached to the nanosensor circuit on the fabric with help of conductive silver ink (such as silver epoxy or polyurethane based silver inks). The finishing of the nanosensor fabric into a wearable garment can be done by lamination, cutting and sewing techniques.

Fabrication of free standing nanostructures on fabric can be achieved by electrostatic or pneumatic deposition (flocking). The deposition is site specific because it is defined by the pattern of adhesive printed on fabric 1. With regard to production of the nano-fibers for deposition, an innovative approach may be used, which comprises depositing polymer nanofiber bundles embedded in a matrix of another polymer followed by dissolving of the matrix polymer to expose the nanofibers can be used. As described above, this two or three component fiber technique is useful for better handling of nanofibers and better penetration of adhesive layer meniscus for deposition of standing nanofibers. The two or three component fibers can be flocked like normal micrometer scale (micro-denier) fibers and a subsequent dissolving step can release the nanofibers, resulting in vertically free standing nanostructures on the textile. Composite fibers are best suited because they can be flocked as micro-denier fibers and then bundled polymer nanofibers can be released by dissolving the matrix polymer.

As discussed above, deposition processes can be done in two ways: a) deposition of nanostructured fibers not coated with conductive material, followed by coating of the deposited fibers with conductive material such as silver, gold, platinum, polyaniline, polypyrrole, poly(3,4-ethylenedioxythiophene); (b) deposition with nanostructured fibers pre-coated with conductive material such as silver, gold, platinum, polyaniline, polypyrrole, poly(3,4-ethylenedioxythiophene).

Uncoated composite fibers can be deposited as microfibers on the adhesive coated fabric and then bundled polymer nanofibers can be released by dissolving the matrix polymer. This is followed by metallization of the structures with silver by an electroless plating method. The electroplating process can be performed by a modular electroless plating system with multiple chemical tanks that perform chemical treatment of the nanostructured fiber array. The tanks are glass lined and the dimensions are dependent on the size of conductive textile substrate being used for fabrication. For example, deposited fibers are washed in deionized water and then subjected to chemical treatment. In particular, the chemical treatment may begin with a matrix polymer etch being performed on the nanofiber surface (which is the surface of the composite nanofibers 7 which have been cut, activated, and deposited) to dissolve the matrix polymer and expose embedded nanostructures. The matrix polymer can be dissolved by dipping the nanosensor sheet(s) in a solvent bath (which is, for example, a part of the modular electroless plating apparatus). The embedded nanofibers, by design/chemistry, are immiscible in the solvent. After dissolution of the matrix polymer, the embedded nanofibers are exposed. The nanofiber surface is then cleaned. Vertically free standing nanofibers on textile substrate are achieved in this manner to achieve a textile based nanosensor. These nanosensors are now ready for coating of conductive or any other functional film as described in this application. The nanofiber surface is primed for plating with $Sn^{2+}$ colloidal bath. The nanofiber surface is then dip coated with silver plating ink and then the ink is dried to form silver film on nanofibers in nitrogen environment in excess of 60° C. Then, the silver film is annealed at a temperature in excess of 100° C. to improve attachment to the nanofiber surface. At this point in the process, conductive nanosensors have been produced. Then, conformal coating of the nanosensor surface is performed with dielectric polymer film such as poly 4-vinyl phenol. Conformal coating may, for example, be performed with a 360° spray coating nozzle such as a BETE MicroWhirl nozzle. Then the film is cured in a convection oven, for example, in a convection oven with temperature control such as a VWR Gravity Convection oven.

The use of pre-coated nanostructured fibers (also hereinafter "fibers") allows for direct deposition of conductive nanostructures at specific sensor locations on the fabric of the garment. The sensor locations for sensors 2 are selected based on the location of conductive tracks 3 on the fabric 1 as described above in connection with the discussion of FIG. 1.

As noted above, the pre-coating of the nanostructured fibres can be done in two ways: (i) batch spray coating and (ii) coating of vertically freestanding nanostructured fibres on a dissolvable substrate followed by release of the fibres by dissolving the substrate.

Batch spray coating can be performed in a series of processes involving soaking and spraying a batch of freely suspended activated fibres. The process includes the following steps: (i) a matrix polymer etch of the fiber surface to expose embedded nanostructures, (ii) cleaning the fiber surface, (iii) priming the fiber surface for plating by re-suspending fibers in a Sn2+ colloidal bath, (iv) drying and separation of the fibers, (v) passing the fibers on a vibrating sifter tray through a spray coating setup to first moisten the fibers with a mist spray and then spray coating of fiber surface with silver plating ink, (v) drying of the ink to form silver nanoparticle film on fibers in nitrogen environment in excess of 60° C. in a rotating dryer, (vi) annealing of the silver nanoparticle film in excess of 100° C. to improve attachment to the fiber using a radiating oven.

Coating of vertically freestanding fibres on a dissolvable substrate followed by release of the fibres follows many of the same steps as the electroless plating process described above. The activated fibers are deposited on a dissolvable substrate using a high strength electrostatic field of 2 kV/cm-10 kV/cm for deposition of the electrostatically charged fibers as vertically standing fibers. The dissolvable substrate can be a knitted/woven web of very low fiber count or a non-woven and the adhesive can be applied as a very thin film because durability under friction is desired here. The solvent can be a non-polar or a polar solvent different from the solvents used in electroless plating process. This substrate can then be taken through the electroless plating process. The steps of electroless plating include (i) matrix polymer etch on the fiber surface to expose embedded nanostructures, (ii) cleaning the fiber surface, (iii) priming the fiber surface for plating with Sn2+ colloidal bath, (iv) dip coating of fiber surface with silver plating ink, (v) drying of the ink to form silver nanoparticle film on fibers in nitrogen environment in excess of 60° C., (vi) annealing of the silver nanoparticle film in excess of 100° C. to improve attachment to the fiber. The fibers are then release from the substrate using a solvent for the dissolvable substrate. Thus obtaining freely suspended pre-coated fibers. These fibers can then be dried to remove the solvent.

The processes mentioned above can achieve conductive coating on the fibres. The process parameters and volumes can be modified for different functional coatings such as dielectric, piezoelectric, semiconducting etc., and production requirements.

The free standing nanostructured fibers can be coated with film of silver (as described above), or by another conductive material such as gold, platinum, polyaniline, polypyrrole, poly(3,4-ethylenedioxythiophene) to make them electroactive for applications such as but not limited to health monitoring EKG, EEG, EOG, EMG electrode application, touch sensors. They can be coated with metal oxide such as films for capacitive sensing application such as but not limited to respiration rate, air quality, gas sensing, and water quality. They can be coated with piezoelectric material film like polyvinylidene difluoride (PVDF) for application such as but not limited to motion sensing, acoustic transduction, noise dampening, impact sensing.

Figure 9:
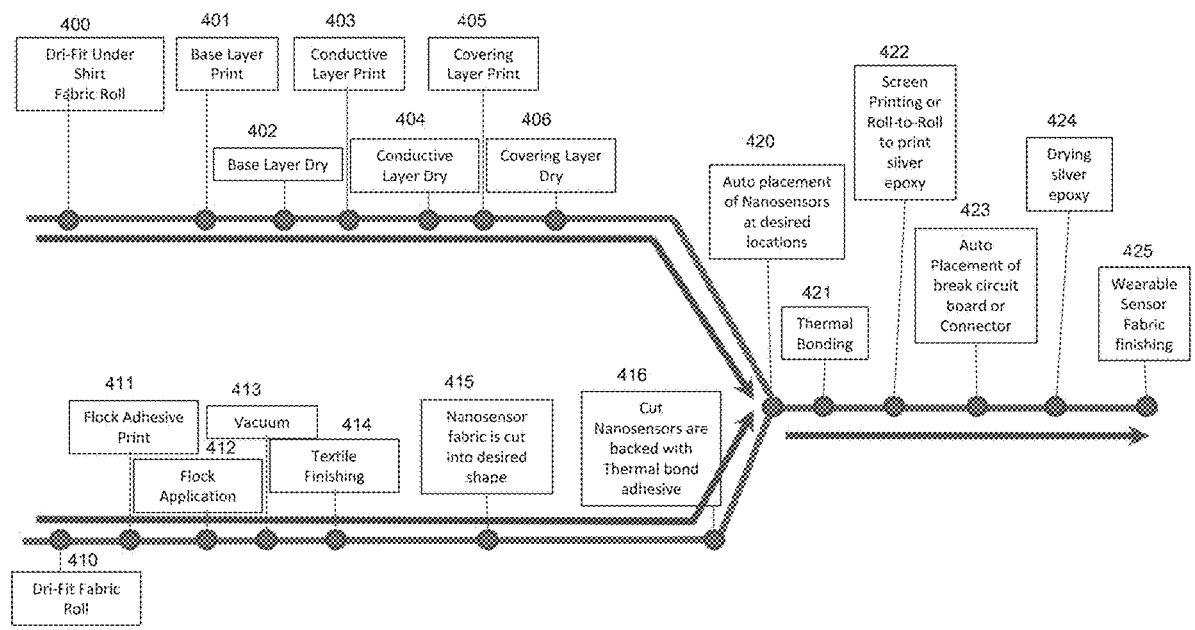
FIG. 9 shows a flowchart for a roll-to-roll process for nanosensor system fabrication including parallel processes for conductive track fabrication and for sensor fabrication.

FIG. 9 shows a roll-to-roll process for nanosensor system fabrication. This includes two parallel processes: one for printing conductive tracks, and the other for sensor fabrication. The printing of conductive tracks follow the process explained in the first stage, and the sensor fabrication process follow the second stage in FIG. 8. The fabricated sensors are cut into required shapes and sizes, and coated with a thermal bind adhesive on its backside. These sensors are placed at precise locations on the fabric using a robotic arm. Similar to the third stage in FIG. 8, the electronics and/or connectors are mounted to the fabric as a final step. The deposition processes can be done in two ways: a) with nanostructured fibers pre-coated with conductive material such as silver, gold, platinum, polyaniline, polypyrrole, poly(3,4-ethylenedioxythiophene) and rendered conductive or b) with nanostructured fibers not coated with conductive material and coated with conductive material later.

In particular, the shirt fabric is fed from the shirt fabric roll (step 400) into the print head 42 for printing of base insulation layer ink (step 401) and then in to the drying unit 43 in step 402. The curing temperature, dependent on the printing ink, can range from 100° C., to 160° C. The fabric is then cooled down for the next print head. The subsequent print heads are conductive ink 44 for the electrical connectivity (step 403) and the covering insulation 46 (step 405), with their respective drying unit 45 and 47 in steps 404 and 406, to complete the conductive inlay.

Nanosensor fabrication gets done separately. The conductive fabric is fed from a fabric roll in step 410 to flock application of silver coated nanostructures fibers 48-50 in step 412, after which, the nanosensors can be cut in to desired shape (step 415). Vacuum removes any un-attached nanostructured fibers from the fabric in step 413, preferably prior to step 415. After adhesive is applied to the back of the cut nanosensors (step 416), the nanosensors can then be mounted on the fabric with pre-printed conductive inlays using surface mounting technique for placement for proper connection with the conductive inlays. In particular, in step 420, the nanosensors are automatically placed at the desired locations using, for example a robotic arm. This is followed by thermal bonding in step 421 to secure the nanosensors to the fabric. Then the break circuit board or connector gets attached to the nanosensor circuit on the fabric with help of conductive silver ink such as silver epoxy. In particular, in step 422, screen printing or roll to roll printing techniques are used to print silver epoxy at the desired location on the fabric. The break-out circuit board or connector is then automatically placed onto the fabric in step 423, for example, via a robotic arm. Then the silver epoxy is dried in step 423 to secure the connector to the fabric. Finishing of the nanosensor fabric into a wearable garment (step 425) can be done by lamination, cutting and sewing techniques.

In the preceding specification the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

What is claimed is:

1. A roll-to-roll printing process for manufacturing a wireless nanosensor monitoring system, comprising:
   continuously unwinding a fabric from a fabric roll;
   printing an insulating base layer onto the fabric;
   printing a conductive track layer on top of the insulating base layer;
   printing an insulating cover layer on top of the conductive track layer;
   printing an adhesive onto the fabric at a location along the conductive track layer and depositing vertically aligned nanostructures on the adhesive to provide a sensor connected to the conductive track layer; and
   continuously winding the printed fabric into a printed fabric roll during all of the printing steps.

2. The method as recited in claim 1 wherein the sensor is printed onto the fabric in an array.

3. The method as recited in claim 1 wherein the vertically aligned nanostructures include one dimensional and three dimensional structures.

4. The method as recited in claim 1 wherein the step of printing the insulating cover layer comprises selectively applying insulation to cover the conductive track layer while leaving the conductive track layer exposed at the location for later placement of the sensor.

5. The method as recited in claim 1 wherein the insulating base layer includes an insulating polymer material.

6. The method as recited in claim 5 wherein the insulating polymer material is selected from the group consisting of poly vinyl, poly acrylate or polyurethane polymer.

7. The method as recited in claim 1 wherein the conductive track layer includes nanoparticles.

8. The method as recited in claim 7 wherein the nanoparticles includes carbon nanotube polymer dispersed in a binder polymer selected from the group consisting of poly vinyl, polyacrylate or polyurethane base binders.

9. The method as recited in claim 7 wherein the nanoparticles include silver nanoparticles.

10. The method as recited in claim 1 wherein the insulating cover layer includes electrically insulating polymer.

11. The method as recited in claim 1 further comprising printing electronics onto the fabric surface and connecting the electronics to the conductive track layer, the electronics being printed using at least one organic semiconductor.

12. The method as recited in claim 11 wherein the at least one organic semiconductor being selected from the group consisting of pentacene, pentacene-carbon nanotube composite, and poly-3hexylthiophene.

13. The method as recited in claim 11 wherein the at least one organic semiconductor is configured as a thin film transistor.

14. The method as recited in claim 1,
wherein the vertically standing nanofibers are comprised of polymer nanofibers embedded in a matrix polymer;
wherein the step of depositing the vertically standing nanofibers includes performing an electrostatic and/or pneumatic assisted deposition process using a high strength electrostatic field of 2 kV/cm-10 kV/cm to electrostatically charge the nanofibers and deposit the electrostatically charged nanofibers as vertically standing nanofiber; and
wherein the method further includes curing the conductive fabric containing the vertically standing nanofibers, and electroless plating the vertically standing nanofibers, the electroless plating including dissolving the matrix polymer on the nanofiber surface to expose embedded nanostructures on filaments, coating the nanofiber surface with a conductive material, and drying the conductive material to form a conductive film on the nanofibers, and annealing the conductive film coated nanofibers.

15. The method as recited in claim 1,
wherein the vertically standing nanofibers are comprised of polymer nanofibers embedded in a matrix polymer, and wherein the vertically standing nanofibers are coated with a conductive material;

wherein the step of depositing the vertically standing nanofibers includes performing an electrostatic and/or pneumatic assisted deposition process using a high strength electrostatic field of 2 kV/cm-10 kV/cm to electrostatically charge the nanofibers and deposit the electrostatically charged nanofibers as vertically standing nanofibers.

16. The method of claim 1, wherein
the step of providing the fabric from the fabric roll includes unrolling a web of fabric from the fabric roll;
the step of printing the insulating base layer onto the fabric includes printing the insulating base layer onto the web with a first gravure printing head and thereafter drying the web having the insulated base layer with a first dryer located downstream of the first gravure printing head;
the step of printing the conductive track layer on top of the insulating base layer includes printing the conductive layer onto the web with a second gravure printing head located downstream of the first dryer and thereafter drying the web having the insulated base layer and the conductive layer with a second dryer located downstream of the second gravure printing head; and
the step of printing the insulating cover layer on top of the conductive track layer includes printing the insulating cover layer onto the web with a third gravure printing head located downstream of the second dryer and thereafter drying the web having the insulated base layer, the conductive layer, and the insulating cover layer with a third dryer located downstream of the third gravure printing head.

17. A roll-to-roll printing process for manufacturing a wireless nanosensor monitoring system, comprising, in parallel:
(a) printing an adhesive onto a plurality of fabric pieces and depositing vertically aligned nanostructures onto the adhesive to provide a plurality of sensors; and
(b) continuously unwinding a fabric from a fabric roll, printing an insulating base layer onto the fabric, printing a conductive track layer on top of the insulating base layer, printing an insulating cover layer on top of the conductive track layer, placing the plurality of sensors along the conductive track layer, connecting the plurality of sensors to the conductive track layer, and continuously winding the printed fabric into a printed fabric roll during all of the printing placing and connecting steps.

18. The method as recited in claim 17 wherein the step of printing the insulating cover layer comprises selectively applying insulation to cover the conductive track layer while leaving the conductive track layer exposed at the location for later placement of the sensor.

19. The method as recited in claim 17 wherein the insulating base layer includes an insulating polymer material selected from the group consisting of poly vinyl, poly acrylate or polyurethane polymer.

20. The method as recited in claim 17 wherein the conductive layer includes nanoparticles.

* * * * *